United States Patent
Katzhendler et al.

(10) Patent No.: US 6,296,873 B1
(45) Date of Patent: *Oct. 2, 2001

(54) ZERO-ORDER SUSTAINED RELEASE DELIVERY SYSTEM FOR CARBAMAZEPHINE DERIVATIVES

(75) Inventors: Ifat Katzhendler; Michael Friedman, both of Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/539,504

(22) Filed: Mar. 31, 2000

Related U.S. Application Data

(63) Continuation-in-part of application No. 09/436,886, filed on Nov. 9, 1999, now abandoned, which is a continuation of application No. 09/012,265, filed on Jan. 23, 1998, now Pat. No. 5,980,942.
(60) Provisional application No. 60/035,892, filed on Jan. 23, 1997.

(51) Int. Cl.[7] ............................. A61K 9/20; A61K 9/22
(52) U.S. Cl. .................. 424/465; 424/464; 424/468; 424/469; 424/484; 424/488; 424/489; 424/499; 424/500; 424/502
(58) Field of Search .................... 424/464, 465, 424/468, 469, 484, 488, 489, 499, 500, 502

(56) References Cited

U.S. PATENT DOCUMENTS

| | | | |
|---|---|---|---|
| 4,857,336 | 8/1989 | Khanna et al. | 424/473 |
| 5,284,662 | 2/1994 | Koparker et al. | 424/473 |

OTHER PUBLICATIONS

P. K. Jensen, et al., Pharmacokinetic Comparison of Two Carbamazepine Slow–Release Formulations, Acta Neurol Scand 82:135–137 (1990).

John Halebian et al., Pharmaceutical Applications of Polymorphism, vol. 58, No. 8, pp 911–929 (1969).

Tsuneo Umeda, et al., Kinetics of the Thermal Transition of Carbamazepine Polymorphic Forms in the Solid State, 1984.

Paavo Kahela, et al., Pharmacokinetics and Dissolution of Two Crystalline Forms of Carbamazepine, International Journal of Pharmaceutics 14:103–112 (1983).

Ensio Laine, et al, Formation of Dihydrate From Carbamazepine Anhydrate in Aqueous Conditions, International Journal of Pharmaceutics, 20:307–314 (1984).

Christopher F. Terrence, et al., Effect of Baclofen Enantiomorphs on the Spinal Trigeminal Nucleus and Steric Similarities of Carbamazepine, Pharmacology 27: 85–94 (1983).

Ensio Lane, et al., Formation of Dihydrate From Carbamazepine Anhydrate in Aqueous Conditions, International Journal of Pharmaceutics 20:307–314 (1984).

Winnie Wai Ling et al., Kinetics of Transition of Anhydrous Carbamazepine to Carbamazepine Dihydrate in Aqueous Suspensions, vol. 80, No. 5 pp. 496–500 (May 1991).

H. Pöhlmann, et al., Polymorphie, Tielchengröβe und Blutspiegelwerte von Carbamazepin, Pharmazie 30, H. 11 pp 709–711 (1975).

Maria Kuhnert–Brandstätter, Thermomicroscopy in the Analysis of Pharmaceuticals, Pergamon Press vol. 45, selected pages, 1971.

Ensio Laine, et al., Pharmacokinetics and Dissolution of Two Crystalline Forms of Carbamazepine, International Journal of Pharmaceutics, 20:307–314 (1984).

Primary Examiner—Thurman K. Page
Assistant Examiner—Lakshmi S. Channavajjala
(74) Attorney, Agent, or Firm—Hana Verny

(57) ABSTRACT

A zero-order sustained-release delivery system for delivery of carbamazepine or a derivative thereof. A polymeric matrix formulation of carbamazepine comprises hydrophilic polymer or hydrophilic/hydropholic polymer mixture which permits carbamazepine or carbamezepine derivative to be released from the polymer matrix in zero-order release kinetics.

19 Claims, 12 Drawing Sheets

01mm 300kV    300E2 2293/95    C-POWD

01mm 300kV 600E2 4082/96 PD-2D

01mm 300kV    300E2    3414/96  CK4MC6H

10mm 300kV    120E2    3416/96  CK4MC6H

ZERO-ORDER SUSTAINED RELEASE DELIVERY SYSTEM FOR CARBAMAZEPHINE DERIVATIVES

This application is a Continuation-in-part of U.S. patent application Ser. No. 09/436,886 filed on Nov. 9, 1999 now abandoned, which is a continuation of application Ser. No. 09/012,265 filed on Jan. 23, 1998, issued as U.S. Pat. No. 5,980,942 on Nov. 9, 1999, which is based on and claims priority of provisional application Ser. No. 60/035,892, filed on Jan. 23, 1997.

BACKGROUND OF THE INVENTION

1. Field of Invention

This invention concerns a zero-order sustained release drug delivery system suitable for administration of carbamezepine and carbamezepine derivatives released by zero-order kinetics. In particular, the invention concerns the drug delivery system comprising a polymer matrix made of a hydrophilic polymer or a mixture thereof and a pharmaceutically active agent carbamezepine or carbamezepine derivative incorporated into the polymer matrix. The polymer or the polymer mixture forms the matrix for incorporation of carbamezepine or carbamezepine derivative released from the polymer matrix by zero-order release kinetics.

BACKGROUND ART AND RELATED ART DISCLOSURES

Carbamezepine is a well-established antiepileptic compound. It is regarded as a first-line drug in the treatment of patients suffering from partial seizures, with and without second generalization, and in patients with generalized tonic clonic seizures (Porter, R. J., Penry, J. K., pp. 220–231, *Advances in Epileptology*, Meinardi, H., Rowan, A. J., Eds., Swets & Zeitlinger, Amsterdam (1977) and *Acta Neurol. Scand.*, 64, Suppl. 88 (1981)). Besides being an antiepoleptic compound, carbamazepine has also proved effective in the treatment of trigeminal neuralgia and in patients suffering from manic depressive episodes (*Neurol. Neurosurg. Psychiat.*, 29:265–267 91966); *Arch. Neurol.*, 19:129–136 (1968); *Excerpta Medica*, 139–147 (1984); and *Excerpta Medica*, 93–115, (1984)).

Although the half-life of carbamazepine is relatively long, between 25 and 85 hours, after a single dose due to autoinduction, its effect is substantially reduced after repeated dosing (*J. Clin. Pharmacol.*, 23:241–244 (1982); *J. Ther. Drug Monit.*, 3:63–70 (1981); and *Europ. J. Clin. Pharmacol.*, 8:91–96 (1975)). Due to its increased metabolism, pronounced daily fluctuations in the serum concentration of carbamazepine were observed and are of concern.

Because there is a correlation between peak concentrations of carbamazepine and central nervous system (CNS) side effects, especially in patients receiving polytherapy (*Epilepsia*, 28:507–514 (1987); *Epilepsia*, 28:286–299 (1987); *Epilepsia*, 21:341–350 (1980); *Epilepsia*, 25:476–481 (1984) and *Arch. Neurol.*, 41:830–834 (1984)), it is of great clinical importance to assure a steady level of carbamazepine during a 24-hour carbamazepine delivery.

Using conventional carbamazepine formulations, however, this can only be achieved by dividing the total daily intake into several, typically 3–4 doses per day. This is very bothersome for ambulatory patients and laborious for medical personnel in institutions and may, therefore, result in compliance problems.

The availability and introduction of slow release carbamazepine formulations would be, therefore, regarded as a major clinical advantage. To date, such formulation has not been available, mainly due to physical and chemical properties of carbamazepine.

It is well known that differences due to polymorphism and pseudopolymorphism observed in certain pharmaceuticals are of importance because physical and chemical properties of different crystalline forms of these pharmaceuticals vary. Differences in these chemical or physical properties, such as for example, solubility, can affect their bioavailability and effective clinical use (*J. Pharm. Sci.*, 58:911–929 (1969)).

Several polymorphs of carbamazepine have been described in *Thermomicroscopy in the Analysis of Pharmaceuticals*, Pergamon, N.Y., p. 227 (1971); *Pharmazie*, 11:709–711 (1975); and *Yakaguku Zasshi*, 104:786–792 (1988). Pseudopolymorphs, such as the dihydrate solvate and an acetone were disclosed in *Int. J. Pharm.*, 14:103–112 91983); *Int. J. Pharm.*, 20:307–314 (1984); and *Pharmacology*, 27:85–94 (1983).

In the presence of water, carbamazepine is known to transform rapidly to carbamazepine dihydrate. Carbamazepine dihydrate crystals grow by the whisker mechanism (*Int. J. Pharm.*, 20:307–314 (1984)) and conversion has been shown by x-ray powder diffraction to be 95% complete after 1 hour (*J. Pharm. Sci.*, 80:496–500 (1991)).

The inhibition of formation of large crystals of carbamazepine dihydrate are of great importance for its pharmaceutical formulation since the formation of large crystals of carbamazepine dissolve slowly and unpredictably and, therefore, cause bioavailability problems and may result in unpredictable and uncontrollable drug delivery.

Some attempts to overcome the above problems were made. For example, Khanna S. C., et al., U.S. Pat. No. 4,857,336, have described an oral dosage form for administration of carbamaepine wherein a core comprising a paste of a fine carbamazepine powder dissolved in a protective colloid, a .hydrophilic swelling agent and, optionally, a water-soluble osmosis inducing-agent was encapsulated in a water-permeable shell impermeable to the components of the core. The water-permeable encapsulation shell permits a water passage through the cell for the transport of the water soluble core components into the surrounding aqueous body fluid. However, in this arrangement the delivered amount is not strictly controllable because it depends on the amount of water present in the surrounding environment, on the permeability of the shell to the water and on the overall kinetics of carbamazepine release from the colloid and its transport through the shell. Additionally, the manufacturing of the past masses is inconvenient and laborious due to the need for encapsulation and additionally requires use of organic solvents which may affect the drug properties.

In an attempt to solve the above problems, the U.S. Pat. No. 5,284,662, has improved the oral formulation for delivery of carbamazepine by reducing the usage of the organic solvents, particularly in core preparations, thus avoiding possible formation of unsuitable pasty masses in manufacture and resulting in somehow easier processing. However, similarly to the above described formulation, this formulation does not eliminate or inhibit crystallization and therefore also results in unpredictable drug delivery.

The primary aim of this invention is to provide a controllable, predictable and true zero-order release dosage formulation of carbamazepine or a carbamazepine derivative released by zero-order kinetics using a simple, fast, easy and more practical manufacturing process than those currently available and described in the two patents cited above.

The delivery system of the invention comprises carbamazepine or a carbamazepine derivative formulated as an erodible tablet or other oral formulation based on a polymeric matrix of a hydrophilic polymer or a combination of a hydrophilic and a hydrophobic polymer containing carbamazepine or a carbamazepine derivative. The polymer matrix permits zero-order release kinetics of the drug.

All patents, patent applications or publications cited herein are hereby incorporated by reference.

SUMMARY

One aspect of the invention relates to a controlled-release oral drug delivery system comprising, as an active ingredient, a pharmaceutical agent carbamazepine or a derivative thereof, which is formulated within a polymeric matrix comprising a hydrophilic, or a mixture of hydrophilic and hydrophobic polymer, said system optionally further containing additional pharmaceutically acceptable constituents, wherein the pharmaceutical agent is released from said matrix by zero-order kinetics.

Another aspect of the invention is an erodible tablet for controlled-release oral drug delivery comprising carbamazepine or a carbamazepine derivative formulated within a polymeric matrix comprising hydrophilic or a mixture of hydrophilic and hydrophobic polymer according to the invention.

Yet another aspect of the invention is an erodible tablet comprising carbamazepine or a carbamazepine derivative, a hydrophilic polymer, a mixture of hydrophilic polymers or a mixture of hydrophilic and hydrophobic polymers alone or in combination with other pharmaceutically acceptable constituents.

Another aspect of the invention is a polymeric matrix for zero-order release kinetics of a pharmaceutical agent comprising a hydrophilic polymer, a mixture of hydrophilic polymers or a mixture of hydrophilic and hydrophobic polymers alone or in combination with the other pharmaceutically acceptable constituents.

Still another aspect of the invention is a controlled-release drug delivery system wherein carbamazepine or a carbamazepine derivative is released from the matrix at a predictable, controllable, continuous, zero-order release kinetics.

DEFINITIONS

As used herein:

"HPMC" means hydroxypropyl methylcellulose.

"SEM" means scanning electron micrograph.

"DSC" means differential scanning calorimetry.

"Zero-order release rate" or "zero order release kinetics" means a constant, linear, continuous, sustained and controlled release rate of carbamazepine or a carbamazepine derivative from polymer matrix, i.e. the plot of mass of carbamazepine or carbamazepine derivative released vs. time is linear.

"Pharmaceutically active agent", "active drug" or "active ingredient" means carbamazepine or a carbamazepine derivative having low solubility which is released by zero order kinetics. These derivatives are represented by compounds:

10,11-dihydro-10-oxo-5H-dibenz/b,f/azepine-5-carboxamide/(oxcarbazepine);
10,11-dihydro-10-hydroxy-5H-dibenz/b,f/azepine-5-carboxamide;
10-acetoxy-10,11-dihydro-5H-dibenz/b,f/azepine-5-carboxamide;
10-benzoyloxy-10,11-dihydro-5H-dibenz/b,f/azepine-5-carboxamide;
10-(4-methoxybenzoyloxy)-10,11-dihydro-5H-dibenz/b,f/azepine-5-carbomamide;
10-(3-methoxybenzoyloxy)-10,11-dihydro-5H-dibenz/b,f/azepine-5-carboxamide;
10-(2-methoxybenzoyloxy)-10,11-dihydro-5H-dibenz/b,f/azepine-5-carboxamide;
10-(4-nitrobenzoyloxy)-10,11-dihydro-5H-dibenz/b,f/azepine-5-carboxamide;
10-(3-nitrobenzoyloxy)-10,11-dihydro-5H-dibenz/b,f/azepine-5-carboxamide;
10-(2-nitrobenzoyloxy)-10,11-dihydro-5H-dibenz/b,f/azepine-5-carboxamide;
10-(4-chlorobenzoyloxy)-10,11-dihydro-5H-dibenz/b,f/azepine-5-carboxamide;
10-(3-chlorobenzoyloxy)-10,11-dihydro-5H-dibenz/b,f/azepine-5-carboxamide;
10-(2-acetoxybenzoyloxy)-10,11-dihydro-5H-dibenz/b,f/azepine-5-carboxamide;
10-propionyloxy-10,11-dihydro-5H-dibenz/b,f/azepine-5-carboxamide;
10-butyryloxy-10,11-dihydro-5H-dibenz/b,f/azepine-5-carboxamide;
10-pivaloyloxy-10,11-dihydro-5H-dibenz/b,f/azepine-5-carboxamide;
10-[(2-propyl)pentanoyloxy]-10,11-dihydro-5H-dibenz/b,f/azepine-5-carboxamide;
10-[(2-ethyl)hexanoyloxy]-10,11-dihydro-5H-dibenz/b,f/azepine-5-carboxamide;
10-stearoyloxy-10,11-dihydro-5H-dibenz/b,f/azepine-5-carboxamide;
10-cyclopentanoyloxy-10,11-dihydro-5H-dibenz/b,f/azepine-5-carboxamide;
10-cyclohexanoyloxy-10,11-dihydro-5H-dibenz/b,f/azepine-5-carboxamide;
10-phenylacetoxy-10,11-dihydro-5H-dibenz/b,f/azepine-5-carboxamide;
10-(4-methoxyphenyl)acetoxy-10,11-dihydro-5H-dibenz/b,f/azepine-5-carboxamide;
10-(3-methoxyphenyl)acetoxy-10,11-dihydro-5H-dibenz/b,f/azepine-5-carboxamide;
10-(4-nitrophenyl)acetoxy-10,11-dihydro-5H-dibenz/b,f/azepine-5-carboxamide;
10-(3-nitrophenyl)acetoxy-10,11-dihydro-5H-dibenz/b,f/azepine-5-carboxamide;
10-nicotinoyloxy-10,11-dihydro-5H-dibenz/b,f/azepine-5-carboxamide;
10-isonicotinoyloxy-10,11-dihydro-5H-dibenz/b,f/azepine-5-carboxamide;
10-(4-aminobutanoyloxy)-10,11-dihydro-5H-dibenz/b,f/azepine-5-carboxamide;
10-(2-amino-3-methylbutanoyloxy)-10,11-dihydro-5H-dibenz/b,f/-azepine-5-carboxamide;
10-chloroacetoxy-10,11-dihydro-5H-dibenz/b,f/azepine-5-carboxamide;
10-bromoacetoxy-10,11-dihydro-5H-dibenz/b,f/azepine-5-carboxamide;
10-formyloxy-10,11-dihydro-5H-dibenz/b,f/azepine-5-carboxamide;
10-ethoxycarbonyloxy-10,11-dihydro-5H-dibenz/b,f/azepine-5-carboxamide;
10-(2-chloropropionyloxy)-10,11-dihydro-5H-dibenz/b,f/azepine-5-carboxamide;
10,11-dihydro-10-hydroxyimino-5H-dibenz/b,f/azepine-5-carboxamide;
10,11-benzyloxyimino-10,11-dihydro-5H-dibenz/b,f/azepine-5-carboxamide;

10-acetyloxyimino-10,11-dihydro-5H-dibenz/b,f/azepine-5-carboxamide;

10,11-dihydro-10-propionyloxyimino-5H-dibenz/b,f/azepine-5-carboxamide;

10-butyroyloxyimino-10,11-dihydro-5H-dibenz/b,f/azepine-5-carboxamide;

10,11-dihydro-10-pivaloyloxyimino-5H-dibenz/b,f/azepine-5-carboxamide;

10,11-dihydro-10-[(1-napthoyloxy)imino]-5H-dibenz/b,f/azepine-5-carboxamide;

10-benzoyloxyimino-10,11-dihydro-5H-dibenz/b,f/azepine-5-carboxamide;

10,11-dihydro-10-succinoyloxyimino-5H-dibenz/b,f/azepine-5-carboxamide;

10,11-dihydro-10-glutaroyloxyimino-5H-dibenz/b,f/azepine-5-carboxamide;

10,11-dihydro-10-isobutoxycarbonyloxyimino-5H-dibenz/b,f/azepine-5-carboxamide;

10,11-dihydro-10-methoxyimino-5H-dibenz/b,f/azepine-5-carboxamide;

10,11-dihydro-10-(S)-(−)-camphanoyloxyimino-5H-dibenz/b,f/azepine-5-carboxamide;

10,11-dihydro-10-[(3-methoxybenzoyloxyimino)]-5H-dibenz/b,f/azepine-5-carboxamide;

10,11-dihydro-10-nicotinoyloxyimino-5H-dibenz/b,f/azepine-5-carboxamide;

10,11-dihydro-10-ethoxycarbonyloxyimino-5H-dibenz/b,f/azepine-5-carboxamide;

10-butoxycarbonyloxyimino-10,11-dihydro-5H-dibenz/b,f/azepine-5-carboxamide; and 10-benzyloxycarbonyloxyimino-10,11-dihydro-5H-dibenz/b,f/azepine-5-carboxamide.

DETAILED DESCRIPTION OF THE INVENTION

Figure 1A:
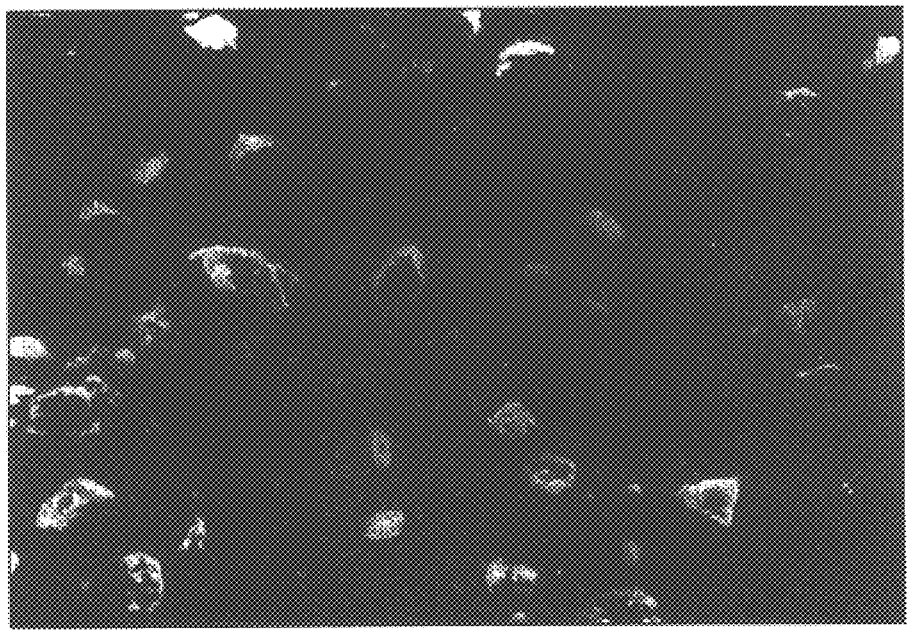
FIG. 1 shows scanning electron micrograph of carbamazepine in anhydrous form (FIG. 1A) and in dihydrate crystals (FIG. 1B).

The present invention relates to a controlled and sustained release oral drug delivery system comprising carbamazepine or a carbamazepine derivative. Carbamazepine or the derivative thereof is formulated within a polymeric matrix, said matrix optionally further containing additional pharmaceutically acceptable constituents and additives. The polymer in the polymeric matrix permits carbamazepine or its derivative to be released from the matrix by zero-order release kinetics.

I. Components of the Oral Drug Delivery System

The drug delivery system of the invention contains at least two components, namely a pharmaceutically active agent and a hydrophilic polymer.

One component of the drug delivery system of the invention is a pharmaceutically active agent. Pharmaceutically active agent is selected from the group consisting of an antiepileptic drug carbamazepine or any of carbamazepine derivative having the same properties.

Carbamazepine derivatives which possess the same or similar zero-order release kinetics properties from the polymer matrix are:

10,11-dihydro-10-oxo-5H-dibenz/b,f/azepine-5-carboxamide/(oxcarbazepine);

10,11-dihydro-10-hydroxy-5H-dibenz/b,f/azepine-5-carboxamide;

10-acetoxy-10,11-dihydro-5H-dibenz/b,f/azepine-5-carboxamide;

10-benzoyloxy-10,11-dihydro-5H-dibenz/b,f/azepine-5-carboxamide;

10-(4-methoxybenzoyloxy)-10,11-dihydro-5H-dibenz/b,f/azepine-5-carboxamide;

10-(3-methoxybenzoyloxy)-10,11-dihydro-5H-dibenz/b,f/azepine-5-carboxamide;

10-(2-methoxybenzoyloxy)-10,11-dihydro-5H-dibenz/b,f/azepine-5-carboxamide;

10-(4-nitrobenzoyloxy)-10,11-dihydro-5H-dibenz/b,f/azepine-5-carboxamide;

10-(3-nitrobenzoyloxy)-10,11-dihydro-5H-dibenz/b,f/azepine-5-carboxamide;

10-(2-nitrobenzoyloxy)-10,11-dihydro-5H-dibenz/b,f/azepine-5-carboxamide;

10-(4-chlorobenzoyloxy)-10,11-dihydro-5H-dibenz/b,f/azepine-5-carboxamide;

10-(3-chlorobenzoyloxy)-10,11-dihydro-5H-dibenz/b,f/azepine-5-carboxamide;

10-(2-acetoxybenzoyloxy)-10,11-dihydro-5H-dibenz/b,f/azepine-5-carboxamide;

10-propionyloxy-10,11-dihydro-5H-dibenz/b,f/azepine-5-carboxamide;
10-butyryloxy-10,11-dihydro-5H-dibenz/b,f/azepine-5-carboxamide;
10-pivaloyloxy-10,11-dihydro-5H-dibenz/b,f/azepine-5-carboxamide;
10-[(2-propyl)pentanoyloxy]-10,11-dihydro-5H-dibenz/b,f/azepine-5-carboxamide;
10-[(2-ethyl)hexanoyloxy]-10,11-dihydro-5H-dibenz/b,f/azepine-5-carboxamide;
10-stearoyloxy-10,11-dihydro-5H-dibenz/b,f/azepine-5-carboxamide;
10-cyclopentanoyloxy-10,11-dihydro-5H-dibenz/b,f/azepine-5-carboxamide;
10-cyclohexanoyloxy-10,11-dihydro-5H-dibenz/b,f/azepine-5-carboxamide;
10-phenylacetoxy-10,11-dihydro-5H-dibenz/b,f/azepine-5-carboxamide;
10-(4-methoxyphenyl)acetoxy-10,11-dihydro-5H-dibenz/b,f/azepine-5-carboxamide;
10-(3-methoxyphenyl)acetoxy-10,11-dihydro-5H-dibenz/b,f/azepine-5-carboxamide;
10-(4-nitrophenyl)acetoxy-10,11-dihydro-5H-dibenz/b,f/azepine-5-carboxamide;
10-(3-nitrophenyl)acetoxy-10,11-dihydro-5H-dibenz/b,f/azepine-5-carboxamide;
10-nicotinoyloxy-10,11-dihydro-5H-dibenz/b,f/azepine-5-carboxamide;
10-isonicotinoyloxy-10,11-dihydro-5H-dibenz/b,f/azepine-5-carboxamide;
10-(4-aminobutanoyloxy)-10,11-dihydro-5H-dibenz/b,f/azepine-5-carboxamide;
10-(2-amino-3-methylbutanoyloxy)-10,11-dihydro-5H-dibenz/b,f/azepine-5-carboxamide;
10-chloroacetoxy-10,11-dihydro-5H-dibenz/b,f/azepine-5-carboxamide;
10-bromoacetoxy-10,11-dihydro-5H-dibenz/b,f/azepine-5-carboxamide;
10-formyloxy-10,11-dihydro-5H-dibenz/b,f/azepine-5-carboxamide;
10-ethoxycarbonyloxy-10,11-dihydro-5H-dibenz/b,f/azepine-5-carboxamide;
10-(2-chloropropionyloxy)-10,11-dihydro-5H-dibenz/b,f/azepine-5-carboxamide;
10,11-dihydro-10-hydroxyimino-5H-dibenz/b,f/azepine-5-carboxamide;
10,11-benzyloxyimino-10,11-dihydro-5H-dibenz/b,f/azepine-5-carboxamide;
10-acetyloxyimino-10,11-dihydro-5H-dibenz/b,f/azepine-5-carboxamide;
10,11-dihydro-10-propionyloxyimino-5H-dibenz/b,f/azepine-5-carboxamide;
10-butyroyloxyimino-10,11-dihydro-5H-dibenz/b,f/azepine-5-carboxamide;
10,11-dihydro-10-pivaloyloxyimino-5H-dibenz/b,f/azepine-5-carboxamide;
10,11-dihydro-10-[(1-napthoyloxy)imino]-5H-dibenz/b,f/azepine-5-carboxamide;
10-benzoyloxyimino-10,11-dihydro-5H-dibenz/b,f/azepine-5-carboxamide;
10,11-dihydro-10-succinoyloxyimino-5H-dibenz/b,f/azepine-5-carboxamide;
10,11-dihydro-10-glutaroyloxyimino-5H-dibenz/b,f/azepine-5-carboxamide;
10,11-dihydro-10-isobutoxycarbonyloxyimino-5H-dibenz/b,f/azepine-5-carboxamide;
10,11-dihydro-10-methoxyimino-5H-dibenz/b,f/azepine-5-carboxamide;
10,11-dihydro-10-(S)-(−)-camphanoyloxyimino-5H-dibenz/b,f/azepine-5-carboxamide;
10,11-dihydro-10-[(3-methoxybenzoyloxyimino)]-5H-dibenz/b,f/azepine-5-carboxamide;
10,11-dihydro-10-nicotinoyloxyimino-5H-dibenz/b,f/azepine-5-carboxamide;
10,11-dihydro-10-ethoxycarbonyloxyimino-5H-dibenz/b,f/azepine-5-carboxamide;
10-butoxycarbonyloxyimino-10,11-dihydro-5H-dibenz/b,f/azepine-5-carboxamide; and
10-benzyloxycarbonyloxyimino-10,11-dihydro-5H-dibenz/b,f/azepine-5-carboxamide.

Carbamazepine derivatives and their preparation has been disclosed in the European Patent Application 96110490.8, filed on Jun. 28, 1996, published on Jan. 1, 1997 and 97108465.2, filed on May 26, 1997, hereby incorporated by reference.

In the drug delivery system of the invention, the drug is present in amount from about 100 mg to about 1,200 mg per tablet, preferably from about 200 mg to about 500 mg per tablet.

The second component of the delivery system is the polymeric matrix comprising at least one hydrophilic polymer but may contain two or more hydrophilic polymers in admixture. When hydrated, the polymer forms a gel layer around the dry tablet core. The matrix of the invention is made of low or high viscosity erodible polymers or mixtures thereof.

Polymers are mixed with drug in a weight ratio of polymer to drug from about 1:99% to about 99:1%, preferably from about 5:95% to about 90:10%, most preferably from about 10:90% to about 80:20%, depending on the viscosity grade of the polymer, on the tablet dimension and shape and on the desired release rate.

The polymer matrix/carbamazepine formulation is preferably fabricated into tablets, capsules or granules for oral use. Rate of carbamazepine release from the tablets is controlled by the erosion mechanism of the polymer from which carbamazepine is released by zero-order kinetics. Examples of hydrophilic polymers which are suitable as the matrix for the zero-order release kinetics delivery system of the invention are hydrophilic cellulose derivatives.

In general, for producing a tablet on an industrial scale, the drug and polymer are granulated alone or in combination as described below. Lubricants, glidents and other additives may be added and the mixture is compressed into tablets.

Preferred hydrophilic cellulose derivatives are methyl cellulose, hydroxypropyl methylcellulose, hydroxyethyl cellulose, hydroxypropyl cellulose, hydroxyethyl methylcellulose, carboxy methylcellulose and sodium carboxy methylcellulose. The most preferred hydrophilic cellulose derivative is hydroxypropyl methylcellulose (HPMC).

HPMC is particularly preferred for use with carbamazepine or a carbamazepine derivative because of very low water solubility of carbamazepine or its derivative. HPMC is available in a low, normal or high viscosity grades. The viscosity of the polymer controls the release rate of the drug from the formulation and affects its zero-order release kinetics. Specific HPMCs which are most suitable for the current formulation are Methocel K100M, K15M, F4M, E4M, K4M, K100LV, K3, E15LV, E15LN, E15CLV, E5O, E5 and E3, commercially available from Colorcon, Orpington, England.

Viscosity grade and molecular weights of various hydrophilic polymers are seen in Table 1.

TABLE 1

| Methocel | Viscosity Grade 2%, 20° C. mPa.s | Number Average Molecular Weight Mn |
|---|---|---|
| E3, K3 | 3 | |
| E5 | 5 | 10,000 |
| E15LV, E15LN, E15SLV | 15 | 15,000 |
| E50 | 50 | 22,000 |
| K100LV | 100 | 26,000 |
| K4M, F4M, E4M | 4,000 | 86,000 |
| K15M | 15,000 | 120,000 |
| K100M | 100,000 | 246,000 |

The polymers useful in the current invention are preferably methocels having viscosity grade from about 3 to about 100,000 mPa•s at 2% of concentration at 20° C. Table 1 lists the suitable HPMCs by their viscosity at 20° C. and by their molecular weight.

The hydrophilic polymers listed in Table 1 are preferred because they allow the zero-order release rate of the active agent from the polymeric matrix formulation, such as an erodible tablet. When the tablet erodes within the digestive system, carbamazepine or its derivatives are released from the matrix in zero-order release kinetics and are readily absorbed.

While the drug/matrix may be formulated into granules, capsules or other solid pharmaceutical compositions, the erodible tablet form is most preferred.

In general, the ratio of drug:polymer is varied depending on the size and shape of the tablet, on the drug amount and drug release rate, and depends also on the molecular weight and viscosity grade of the polymer, which in general will be from about 3 to about 100,000 mPa•s, preferably from about 5 to about 15,000 mPa•s at 2% concentration at 20° C. temperature.

Typically, when the viscosity grade of the polymer is higher, the release of the drug is slower. When the shape of the tablet is flatter, i.e. when the ratio of a tablet diameter to a tablet width is higher, the drug release is faster. Taking these parameters into consideration, the tablet is formulated according to the drug release requirement to be more flat, that is, having a large surface for faster release or more cylindrical, that is, having smaller surface for slower release. Additionally, for slower release of the drug the higher viscosity grade polymer is used and vice-versa.

The polymeric matrix of the drug delivery of the invention may additionally also contain a hydrophobic polymer. Suitable hydrophobic polymers are hydrophobic cellulose derivatives, such as ethyl cellulose, fats, such as glycerol palmitostearate, waxes, such as beeswax, glycowax, castrowax, carnaubawax, glycerol monostearate or stearylalcohol, hydrophobic polyacrlamide derivatives and hydrophobic methacrylic acid derivatives.

When using a hydrophobic polymer, in order to provide zero-order release, such hydrophobic polymer is used only in a mixture of hydrophilic and hydrophobic polymers. In such a mixture, the hydrophobic polymer controls the water penetration rate into the delivery system. Incorporation of hydrophobic polymer into the polymer matrix and the ratio of hydrophilic to hydrophobic polymer thus changes the erosion characteristics of the tablet. The hydrophobic polymer shows down the water penetration into the tablet and thus slows the tablet erosion.

The hydrophobic polymer is added to the hydrophilic polymer in amount from about 0.1 to about 10%, preferably from about 1% to about 5%, of the total polymer. Ratios of hydrophilic to hydrophobic polymer are from about 99.9:0.1 to about 90:10, preferably from about 99:1 to about 95:5.

In one embodiment, the polymeric matrix comprises either a hydrophilic cellulose derivative alone or a mixture of two or more hydrophilic cellulose derivatives. In another embodiment, the polymeric matrix comprises hydrophilic cellulose derivative alone or a mixture of said hydrophilic cellulose derivatives in combination with any one of the above hydrophobic polymers or a mixture of such hydrophobic polymers. In still another embodiment, hydrophilic cellulose derivative or a mixture thereof, in combination with any of said hydrophobic polymers or a mixture of said hydrophobic polymers, may additionally contain other components, such as pharmaceutically acceptable additives and constituents.

The other pharmaceutically acceptable constituents of the polymeric matrix of the drug delivery of the invention are selected from the groups of proteins, arabinogalactans, chitosans, polysaccharides, hydrophilic polyacrylamide derivatives and hydrophilic methacrylic acid derivatives.

Proteins which are suitable as the matrix carriers are, for example, egg albumin, human albumin, bovine alumin, soy protein, gelatin, casein. The protein can be used in the native or denatured state.

Polysaccharides which are suitable are β-cyclodextrans and starch derivatives.

Additionally, the delivery system of the invention optionally contains release accelerating agents, an example of which are polyethylene glycol, salts and surfactants. Other pharmaceutically acceptable accelerating agents may also be added, as known in the art of pharmaceutical sciences. When incorporating a release accelerating agent, the use of polyethylene glycol in the tablet is preferred since it enhances the solubility of carbamazepine and causes enhancement of amorphism of the carbamazepine.

The present formulation may also contain a pharmaceutically acceptable binder. Pharmaceutically acceptable binders suitable for use in the present formulations are selected from those routinely used by formulators and include sucrose, gelatin, acacia, tragacanth, cellulose derivatives, povidone, polyethylene glycols and other binders known to those familiar with pharmaceutical formulations.

If desired, other additives, such as lubricants, stabilizers and glidents, conventionally used for pharmaceutical formulations, may be included in the present formulations.

The formulations of the invention are prepared by procedures known in the art, such as, for example, by the dry or wet method. The method selected for manufacturing affects the release characteristics of the finished tablet. In one method, for example, the tablet is prepared by wet granulation in the presence of either water or an aqueous solution of the hydrophilic polymer or using other binder as a granulating fluid. In alternative, organic solvent, such as isopropyl alcohol ethanol and the like, may be employed with or without water. The drug and polymer may be granulated alone or in combination. Another method for preparation of the tablet which may be used requires using a drug-polymer dispersion in organic solvents in the presence or absence of water. Because carbamazepine or its derivative has very low solubility in water it is advantageous to reduce the carbamazepine particle size, for example, by milling it into fine powder and in this way to control the release kinetics of the drug and enhance its solubility.

The drug delivery of the invention can utilize any suitable dosage unit form. Specific examples of the delivery system of the invention are tablets, tablets which disintegrate into granules, capsules, sustained release microcapsules or any other means which allow for oral administration. These forms may optionally be coated with pharmaceutically acceptable coating which disintegrates in the digestive system.

Such coating may comprise a biodegradable polymer, a coloring and/or flavoring agent or any other suitable coating. The technique of preparing coated tablet, microcapsule or capsule formulations are known in the pharmaceutical sciences.

The amount of carbamazepine, or a derivative thereof, in the formulation varies depending on the desired dose for efficient drug delivery. The actual amount of the used drug is dependent on the patient's age, weight, sex, medical condition, disease or any other medical criteria. The actual drug amount is determined according to intended medical use by techniques known in the art. The pharmaceutical dosage formulated according to the invention may be administered once or more times per day, as determined by the attending physician.

Typically, carbamazepine is formulated in tablets or other pharmaceutical composition in amounts of about 0.001 to about 1 g, preferably from about 0.2 to about 0.8 g of carbamazepine per day for children. For adults, the daily dose is typically from about 0.001 to about 1.2 grams per day. However, some patients receive up to 1.6–2.4 grams daily. Preferably, the daily amount for adults in between about 0.8 and about 1.2 grams per day formulated to be released slowly to maintain therapeutic levels of carbamazepine in patient's blood between about 4–12 $\mu$g/ml. Above this concentration, patients may experience adverse effects.

The daily dose can be formulated in a single tablet or more than one tablet, depending on the daily dose of carbamazepine and the number of times the formulation is to be administered.

Carbamazepine, formulated according to the invention, is delivered once or twice a day, depending on the release kinetics from the tablet. In rare instances, tablets may be formulated for more frequent administration than twice a day.

II. Crystalline Properties of Carbamazepine in Sustained Release Hydrophilic Matrix Tablets Based on Hydroxypropyl Methylcellulose The effect of hydrophilic polymer, represented by hydroxypropyl methylcellulose (HPMC), on the crystal habit properties of carbamazepine in erodible polymeric matrix tablets and in aqueous solutions was investigated using differential scanning calorimetry (DSC), X-ray powder diffraction and scanning electron microscopy (SEM).

The results indicated that HPMC inhibits the transformation of carbamazepine to carbamazepine dihydrate crystals in the gel layer of hydrated tablets and in aqueous solutions, depending on HPMC concentration. HPMC thus seems to participate and seems to be involved in carbamazepine crystallization process and seems to induce amorphism of carbamazepine crystals. While not intended to be bound by any proposed mechanism, obtained results show that the hydrophilic polymer may serve as a template or microsubstrate for nucleation in the crystallization process. The interaction between the drug and polymer may occur by hydrogen bonding where the hydroxyl groups of the polymer attach to the drug at the site of water binding, and inhibit its transformation to the dihydrate form.

Carbamazepine exists in several polymorphic forms of anhydrous carbamazepine and also as two crystalline modifications of carbamazepine dihydrate. Anhydrous carbamazepine seen in FIG. 1A is practically insoluble in water and when suspended in water, it rapidly transforms into large crystals of carbamazepine dihydrate (FIG. 1B).

Figure 1B:
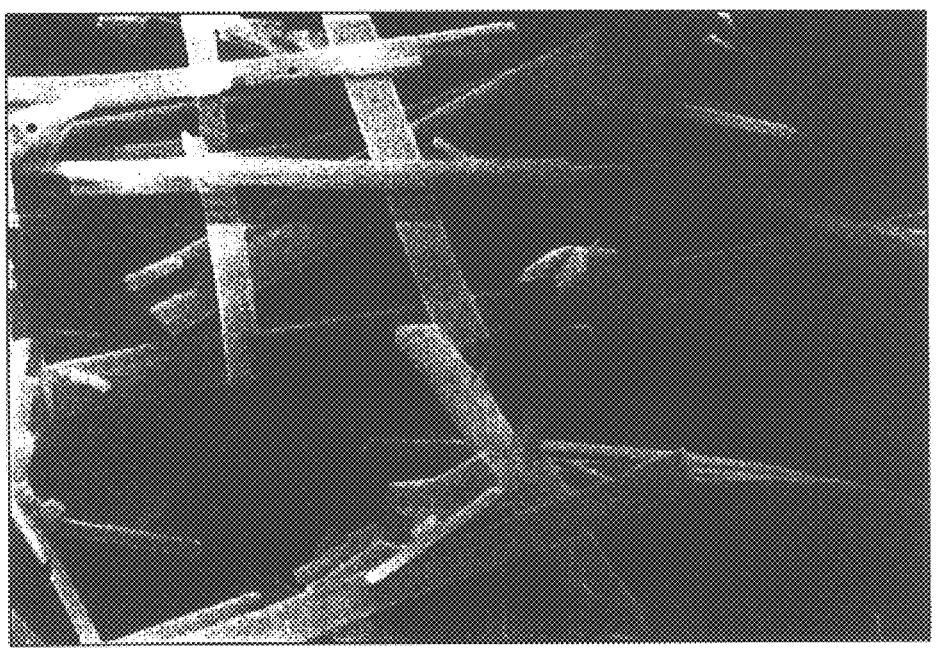
Figure 2A:
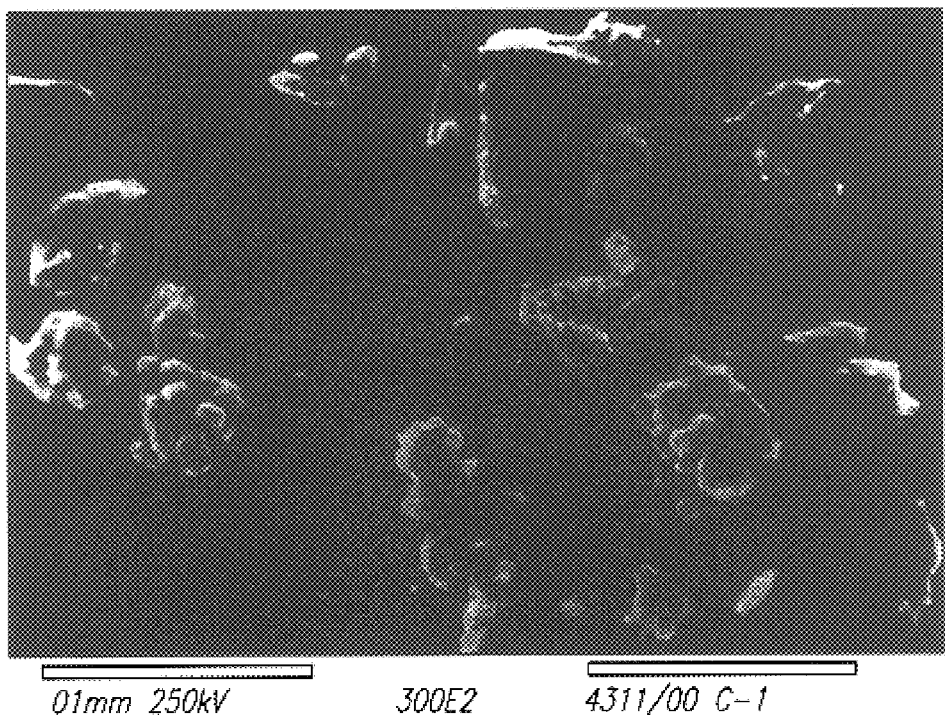
FIG. 2 shows scanning electron micrograph of carbamazepine crystals obtained from suspensions of carbamazepine at different concentrations of Methocel K4M after 1 day at 1 mg/ml (FIG. 2A), at 5 mg/ml (FIG. 2B), at 10 mg/ml (FIG. 2C), and at 7 days at 1 mg/ml (FIG. 2D), 5 mg/ml (FIG. 2E) and at 10 mg/ml (FIG. 2F).
Figure 2B:
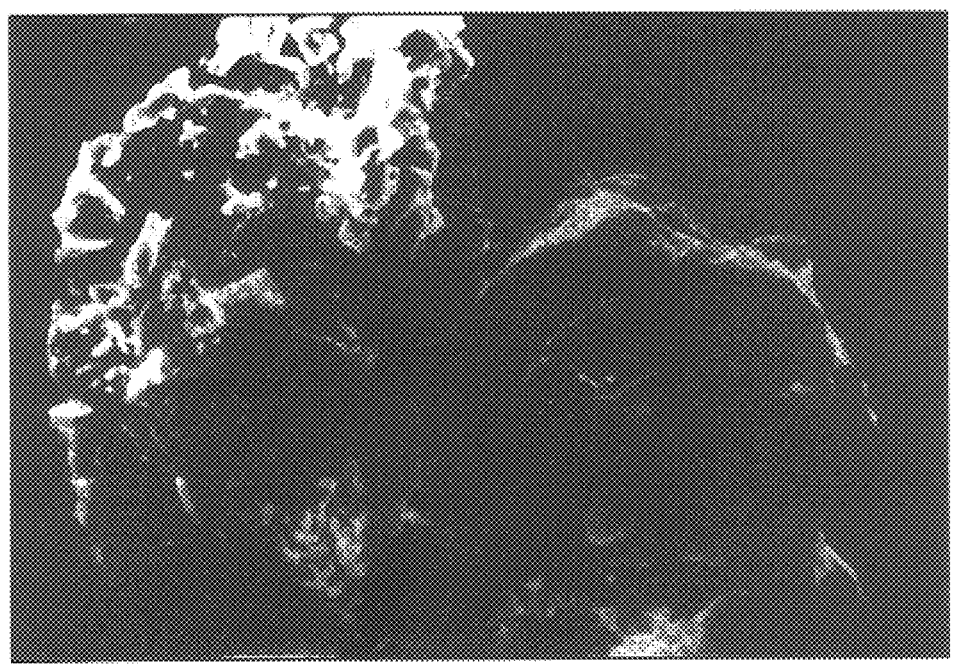
Figure 2C:
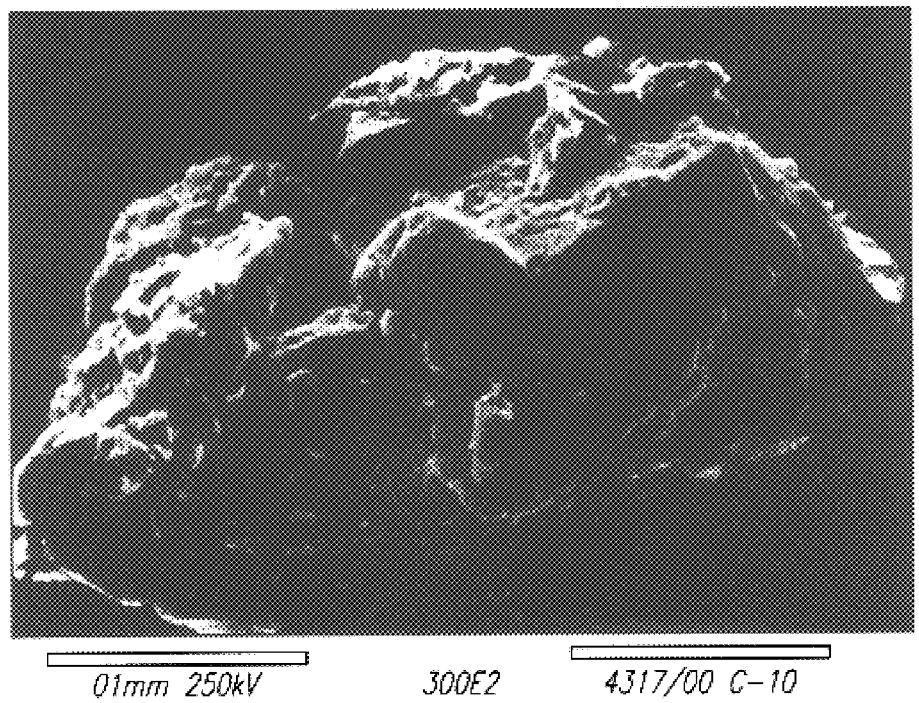
Figure 2D:
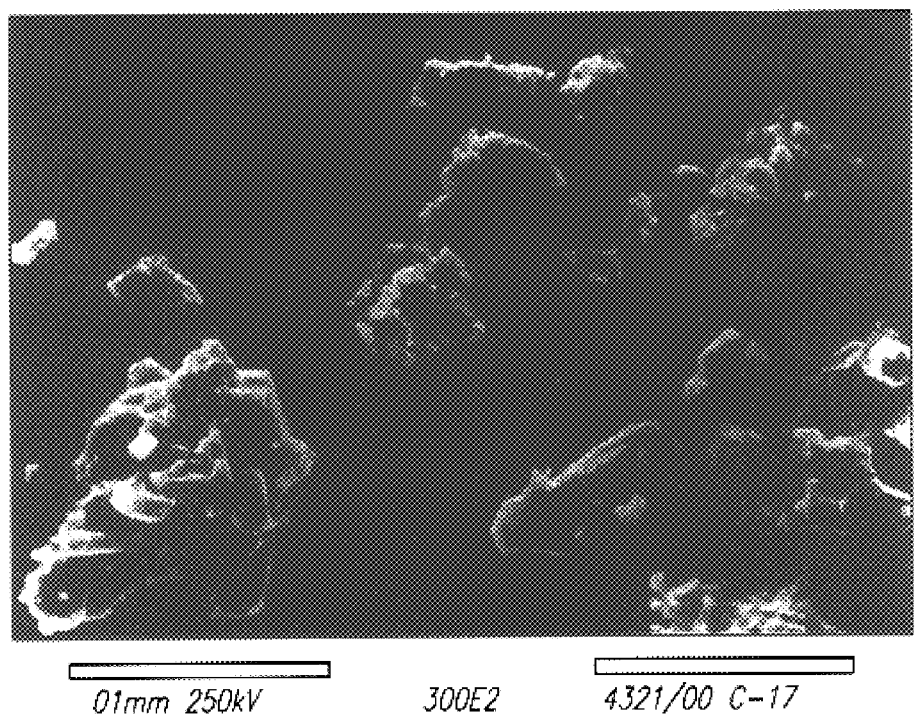
Figure 2E:
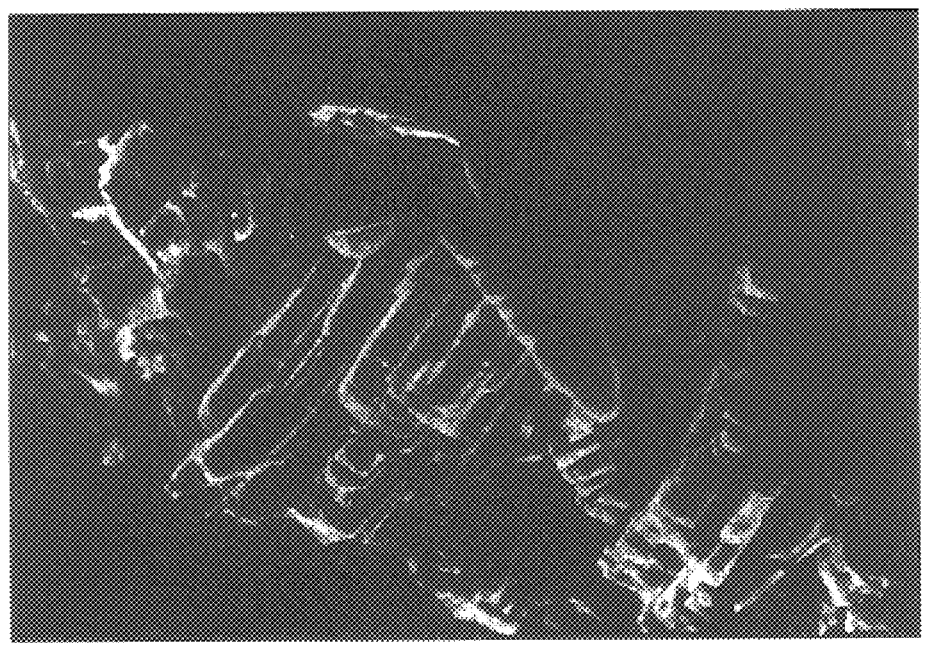
Figure 2F:
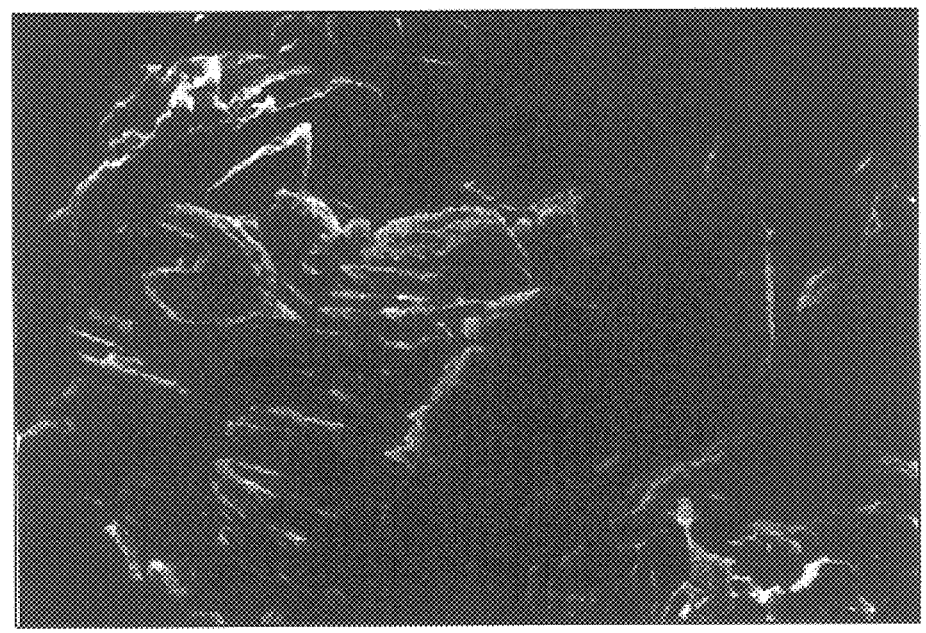

As seen in FIG. 1A, anhydrous crystals are not homogeneous in size and some of them appear as aggregates. When carbamazepine crystals of FIG. 1A are suspended in water, they rapidly form large whisker-shaped crystals. These large whisker-shaped crystals are visible in FIG. 1B.

The thermograms of the anhydrous carbamazepine form measured by differential scanning calorimetry (DSC) revealed that anhydrous carbamazepine was completely converted to dihydrate.

The above discussed properties greatly affect carbamazepine utility as a pharmaceutical drug of choice for treatment of epilepsy and trigeminal neuralgia. Polymorphic forms and/or crystalline forms of carbamazepine change the physical and chemical properties, such as solubility of the drug, the drug bioavailability and its release from the formulations. In order to provide a formulation which assures a steady, continuous, linear, zero-order release rate, the polymeric matrix of specific properties was designed. The properties of various polymers on the release rate of carbamazepine were determined.

Since the carbamazepine readily forms dihydrate crystals, the investigation of these crystal properties were undertaken wherein a conversion of carbamazepine into carbamazepine dihydrate was determined and influence of hydrophilic polymers on such conversion was investigated both in solutions or in the gel layer of hydrated tablets.

For the below described studies, materials were obtained as follows. Carbamazepine was obtained from Taro, Herzliya, Israel. Carbamazepine derivatives are obtained as described in the EP 96110490.8 and EP 97108465.2 applications, referenced above. Three viscosity grades of hydroxypropyl methylcellulose (HPMC), namely Methocel K100LV, Methocel K4M and Methocel K100M were obtained from Colorcon, Orpington, England. Sodium dodecyl sulfate (SDS) was purchased from BDH Poole, England.

Carbamazepine (200 mg) was mixed with HPMC using a pestle and a mortar in ratio as indicated, and the erodible tablets were prepared.

Cylindrical tablets were prepared by direct compression of carbamazepine-polymer blends, using a laboratory press fitted with a 10 mm flat-faced punch and die set, and applying a pressure of 567 MN/m$^2$. All tablets contained 200 mg carbamazepine, unless otherwise indicated. The effect of HPMC on the crystal habit of carbamazepine was examined in formulating containing 50% Methocel K100LV, 50% Methocel K4M and/or 50% Methocel K100M.

The dissolution rates of the tablets were monitored using a tablet dissolution tester (model 7ST Caleva, USA). The USP Basket Method I was used. Rotation speed was 100 rpm, and dissolution medium was 700 ml of 1% SDS aqueous solution (in order to provide sink conditions), maintained at 37° C. Carbamazepine levels were monitored at 288 nm spectrophotometrically using Uvikon 930 Kontron spectrophotometer, obtained from Kontron, Switzerland. Dissolution studies were performed in triplicate for each batch of tablets.

Suspensions of carbamazepine (5% w/v) containing water or 1% SDS aqueous solution were shaken at 37° C. with stirring (50 rpm). Samples from the sediment were taken after 1 day, dried at room temperature for 2 days, and analyzed by differential scanning calorimetry, X-ray powder diffraction and scanning electron microscopy (SEM). Carbamazepine anhydrous powder was analyzed using the same methods.

Analysis of carbamazepine in HPMC solutions and in dry mixtures of HPMC was performed. Suspension of carbamazepine (5% w/v) containing 1% SDS aqueous solution with Methocel K4M at different concentrations, namely 0.5, 1, 2, 5 and 10 mg,/ml were shaken for 1–7 days at 37° C. with stirring (50 rpm). Samples from the sediment were taken, at various time intervals, dried at room temperature for 2 days and analyzed by DSC, X-ray powder diffraction and SEM.

The degree of conversion of anhydrous carbamazepine to the dihydrate form, measured by DSC, was calculated according to the ratio obtained from the dehydration enthalpies of carbamazepine suspended in 1% SDS aqueous Methocel solution and 1% SDS aqueous solution without Methocel. Dry mixtures containing different ratios of HPMC (Methocel K4M) and carbamazepine were also analyzed by DSC in order to investigate the influence of HPMC on the polymorphic transformation of carbamazepine.

Gel layers of the tablets were analyzed. Tablets were hydrated using the USP Basket Method I under the same conditions described in the dissolution studies. At various time intervals the tablets were removed from the baskets, the gel layer was scratched and dried at room temperature for at least 24 hours. The gel layer was analyzed by DSC, X-ray powder diffraction and scanning electron microscopy (SEM). Used analytical methods are described in Example 4.

As discussed above, the release of the drug from large dihydrate crystals is unpredictable due to their changing chemical and physical properties, several alternative conditions affecting such conversion were investigated in suspensions and also in solid tablet forms.

FIGS. 2A–F show the respective SEM photographs of carbamazepine crystals obtained after 1 and 7 days from HPMC solutions containing different concentrations, such as 1 mg, 5 mg or 10 mg/ml of HPMC. As seen in FIG. 2, HPMC has a significant influence on the morphology of the crystals. The crystals obtained from HPMC solutions appear to be amorphous. At a concentration of 1 mg/ml polymer, the precipitate is seen as an aggregate composed of small crystals. At higher concentrations of polymer the precipitate appears as an aggregate composed of smaller crystals adhering to larger ones. Even after 7 days the carbamazepine dihydrate crystals formed had a deformed structure compared with carbamazepine dihydrate solution without HPMC which was in the form of well-developed whisker-shaped crystals as seen in FIG. 1B.

The X-ray diffraction patterns (data not shown) of carbamazepine crystals obtained from Methocel K4M solutions at HPMC concentrations of 1 and 10 mg/ml after 1 day revealed an amorphous structure as indicated by the broader peaks compared with the strong reflections of carbamazepine anhydrous powder. The X-ray diffraction patterns of carbamazepine obtained from 1 mg/ml HPMC solution indicated that the sample consisted of a mixture of carbamazepine and carbamazepine dihydrate crystals while the crystals obtained from 10 mg/ml HPMC solutions contained solely the anhydrous form, thus supporting SEM results seen in FIGS. 2A and 2C.

The DSC thermograph (data not shown) of HPMC Methocel K4M powder revealed a slight change in baseline at 145° C., which is characteristic of the glass transition temperature. This transition could be detected more clearly at a low heating rate of 0.5° C./min. A broad endothermic peak was observed at 0–100° C. which is attributed to the water absorbed on the polymer. No indication of crystallinity was recorded in the thermogram. The polymer was therefore considered amorphous.

Formulations containing Methocel K100LV and K100M, analyzed by SEM, DSC and X-ray, in the same way as described for Methocel K4M revealed the same behavior.

Results are summarized in Tables 2 and 3.

Table 2 shows the influence of Methocel K4M concentration on the degree of conversion of carbamazepine to carbamazepine dihydrate after 24 hours.

TABLE 2

| Methocel K4M concentration (mg/ml) | Degree of Conversion (%) |
| --- | --- |
| 0 | 100 |
| 0.5 | 77.0 |
| 1 | 23.1 |
| 2 | 0 |
| 5 | 0 |
| 10 | 0 |

Table 2 shows that after 24 hours at HPMC concentration of 2 mg/ml and higher, carbamazepine did not convert to dihydrate. At concentrations of 1 mg/ml and lower, Methocel K4M inhibited the transformation to carbamazepine dihydrate only partially. The degree of conversion thus depended on Methocel K4M concentration. After 7 days, as seen in Table 3, carbamazepine was transformed completely to dihydrate at all examined concentrations.

Table 3 shows degree of conversion of carbamazepine to carbamazepine dihydrate in solution containing 5 mg/ml Methocel K4M as a function of time.

TABLE 3

| Time (days) | Degree of conversion (%) |
| --- | --- |
| 1 | 0 |
| 2 | 0.97 |
| 3 | 8.8 |
| 4 | 21.5 |
| 7 | 100 |

Table 3 shows that the transformation of carbamazepine to the dihydrate form is time-dependent.

Similarly to the above described investigation performed in solutions of carbamazepine in the presence and absence of hydrophilic polymers, studies were performed to determine carbamazepine crystal properties in Methocel K4M/carbamazepine power mixture and in hydrated solid tablet forms. Results of these studies are seen in FIGS. 3 and 4.

Figure 3:
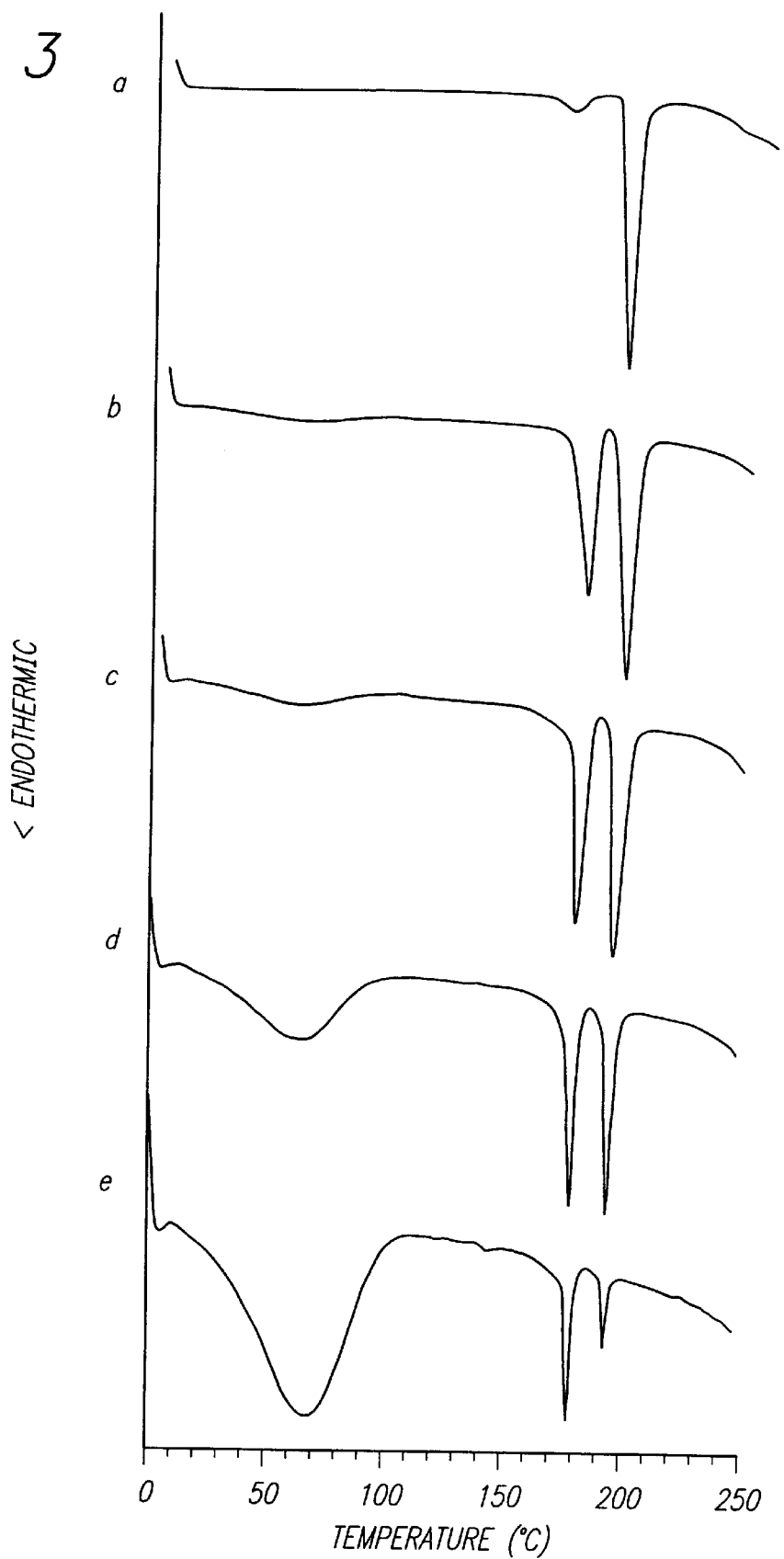
FIG. 3 shows differential scanning calorimetry thermographs of dry mix of Methocel K4M and carbamazepine mixtures in polymer drug ratios 0:100 (FIG. 3A), 20:80 (FIG. 3B), 30:70 (FIG. 3C), 50:50 (FIG. 3D), 80:20 (FIG. 3E).

FIGS. 3A–E presents the DSC thermographs of dry mixtures of Methocel K4M and carbamazepine in different ratios of 0:100 (FIG. 3A), 20:80 (FIG. 3B), 30:70 (FIG. 3C), 50:50 (FIG. 3D) and 80:20 (FIG. 3E). As seen in FIG. 3, carbamazepine exhibited a small endothermic peak at 170.4° C. which is characteristic of the transition of the β-form to the α-form. This transition occurs by solid-solid transformation. The increase of the endothermic peak at 170.4° C. with increasing HPMC concentration in HPMC-carbamazepine mixtures indicates that HPMC alters the transformation mode of the β-form to the α-form. The transition occurs by solid-liquid transformation, with a minimum at 177° C. and a decrease in the enthalpy of melting of the α-form at 192.5° C. This decrease indicates that part of the β-form melted at 177° C. and did not convert to the α-form. The endothermic peak at 177° C. was dependent on HPMC concentration in the mixture. Only a fraction of the β-form converted to the α form by solid-solid transformation, and melted at 192.5° C. This explains the decrease in the enthalpy of melting at 192.5° C. The broad peak that appears at 20–100° C. is related to the water adsorbed to the polymer.

Figure 4:
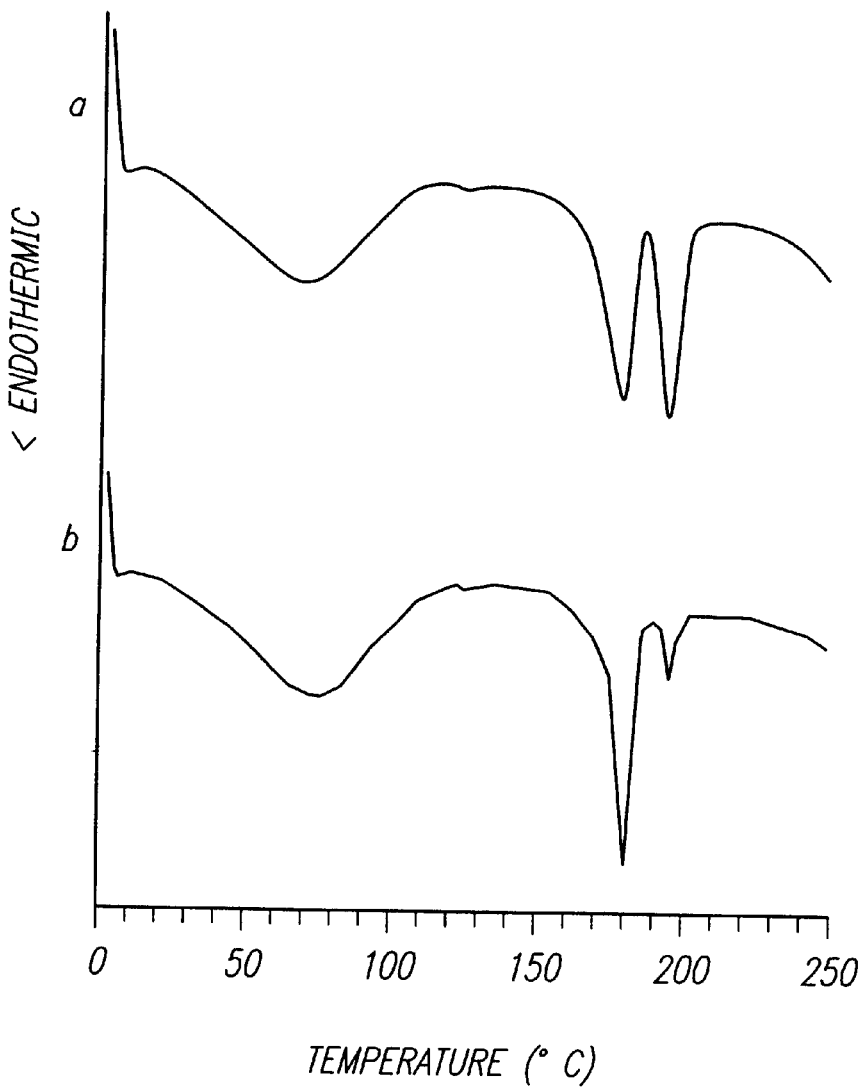
FIG. 4 shows differential scanning calorimetry thermographs obtained from the gel layer of formulation containing 50% Methocel K4M at two hydration times—6 hours hydration (FIG. 4A) and 20 hours hydration (FIG. 4B).

FIGS. 4A and 4B present the DSC thermograms of samples obtained from the gel layer of the hydrated tablets containing 50% polymer after 6 and 20 hours. As seen in FIG. 4, in the gel layer of hydrated tablets the transformation of carbamazepine to the dihydrate form is inhibited. Such inhibition is indicated by the broad peak that appears at 20–100° C. The broad peak is attributed to water absorbed to the polymer and not to the dehydration of carbamazepine dihydrate which appears as a sharp peak with minimum at 80° C.

As seen from the DSC analysis shown in FIGS. 4A and 4B, HPMC inhibited the transformation of carbamazepine to carbamazepine dihydrate in the gel layer. The broad peak obtained at 20–100° C. is related to water adsorbed to the polymer and not to the carbamazepine dihydrate form which is characterized by a sharp peak at 80° C. The increase of the endothermic peak at 178° C. is related to the influence of HPMC on the polymorphic transition of the β-form to the α-form which induces solid-liquid transformation. The X-ray patterns of carbamazepine in the gel layer had peak reflections similar to the X-ray pattern of anhydrous carbamazepine, further supporting the conclusion that HPMC inhibits the transformation of carbamazepine to carbamazepine dihydrate in the gel layer. The X-ray diffraction of the gels reveals that HPMC induces amorphism of carbamazepine. The broad peaks obtained compared with the X-ray patterns of anhydrous carbamazepine crystals and 50:50/HPMC:carbamazepine physical mixture, points to a change in the crystallinity of carbamazepine with the formation of less ordered structure and amorphous appearance.

The above results are further supported by the SEM photographs of carbamazepine crystals in the gel layer seen in FIG. 5 which reveal spherulite morphology with less organized crystal structures and amorphous appearance.

Figure 5A:
FIG. 5 shows scanning electron micrograph photographs obtained from cross section in the gel layer of formulation containing 50% Methocel K4M after 6 hours hydration. Magnification in FIG. 5A is X300.
in FIG. 5B it is X1200.
Figure 5B:
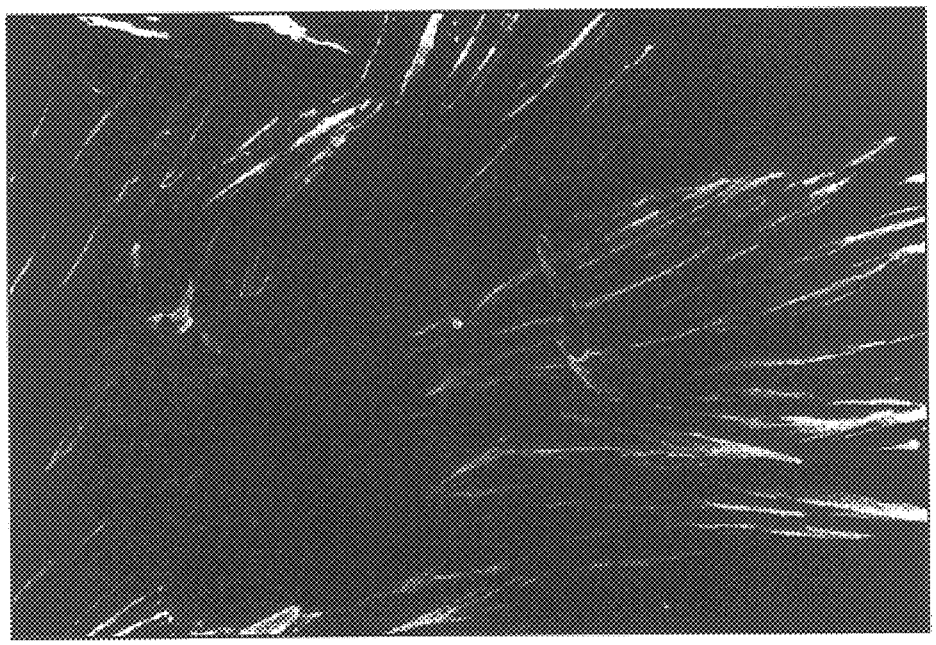
Figure 6:
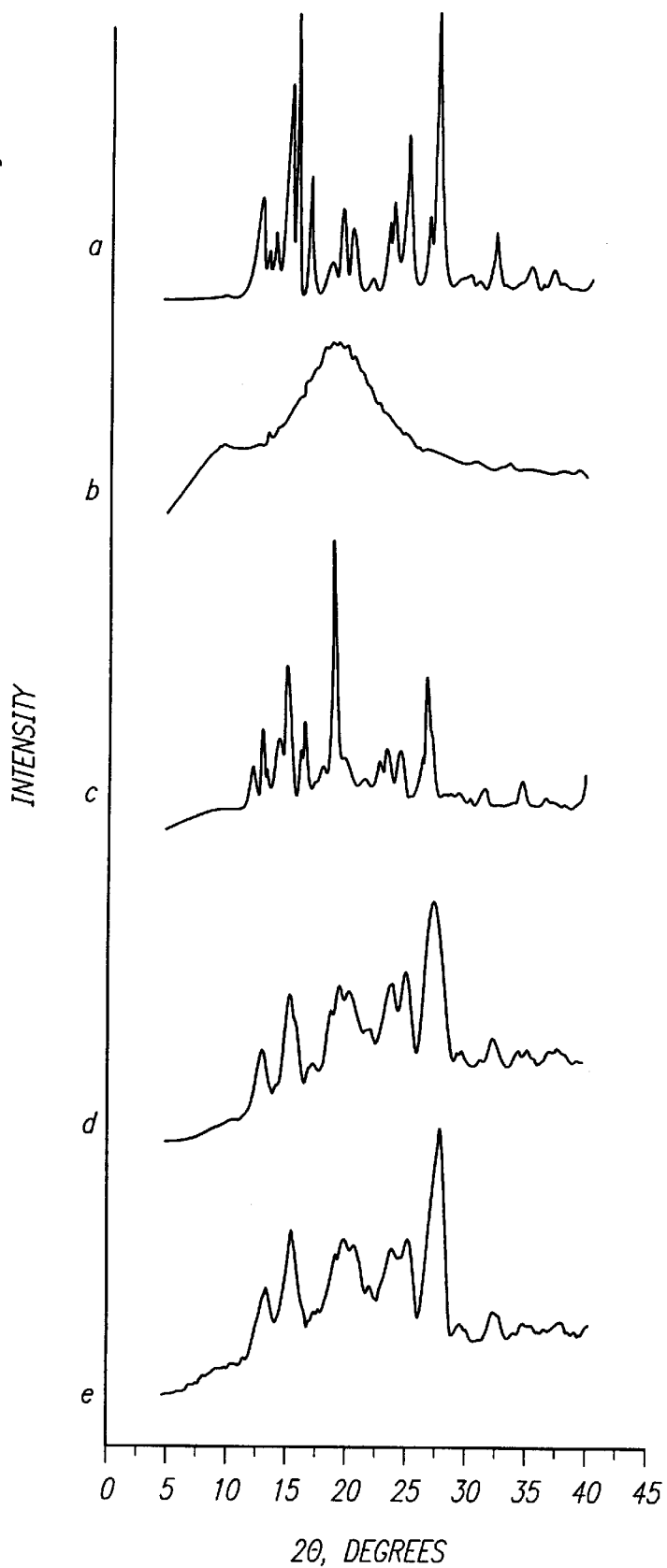
FIG. 6 shows X-ray diffraction patterns of carbamazepine powder (FIG. 6A); Methocel K4M powder (FIG. 6B); 50:50 physical mixture of carbamazepine and Methocel K4M (FIG. 6C); sample from gel layer, 6 hours hydration (FIG. 6D); and sample from gel layer, 20 hours hydration (FIG. 6E).

FIG. 5 presents the corresponding SEM photographs to thermograms seen in FIGS. 4A and 4B, obtained after 6 hours of hydration of carbamazepine (FIG. 5A). As seen in FIG. 5A, carbamazepine in the gel had transformed to an amorphous form. Tablets hydrated for 20 hours showed the same behavior, as seen in FIG. 5B.

FIGS. 6A–E present the respective X-ray diffraction patterns of the gel samples compared with carbamazepine powder, Methocel K4M powder, and 50:50 polymer-drug physical The DSC, X-ray and SEM results (FIGS. 4, 5, and 6), both in solution and in the tablet gel layer, indicate an interaction between carbamazepine and the polymer. These results are also supported by the DSC results of carbamazepine-HPMC dry mixtures.

From the above described results, it is clear that hydrophilic polymers, such as HPMC, inhibit the transformation of carbamazepine to carbamazepine dihydrate in the gel layer, participate in its crystallization process and induce carbamazepine amorphism. The polymer herein may serve as a template or microsubstrate for nucleation in the crystallization process. The interaction between the drug and polymer appears to occur by hydrogen bonding. The hydroxyl groups of the polymer apparently attach to the drug at the site of water binding, and thus its transformation to the dihydrate form in inhibited.

The crystalliztion process which occurs at the gel layer is of major importance when dealing with absorption characteristics of the drug since differences in properties of polymorph, crystallinity and solubility affects the release and bioavailablility of the drug. Since HPMC induces amorphism of the drug and inhibits its transformation to the dihydrate form, it also affects its solubility in water or other media because amorphous crystals dissolve faster than highly crystalline ones. In the process of the invention, the bioavailablility of the drugs is improved and the continuous and linear zero-order release kinetics is assured.

III. Effect of Various Conditions on Carbamazepine Dissolution Rate

Effect of various conditions such as HPMC concentration, viscosity grade of the polymer, additives, rotations speed of baskets, incorporation of PEG 4,000, PEG 20,000 and NaCl to the matrix, SDS concentration in the dissolution medium, etc., on release rate of carbamazepine from the tablets was also investigated. Results are described in FIGS. 7–15.

A. The Effect of HPMC Concentration on Drug Release Rate from the Matrix and on the Dissolution Rate Matrices containing Methocel K4M and carbamazepine were prepared as described above and in Example 2 for preparation of tablets. The polymer concentrations in the matrix were 10–80% w/w.

Figure 7:
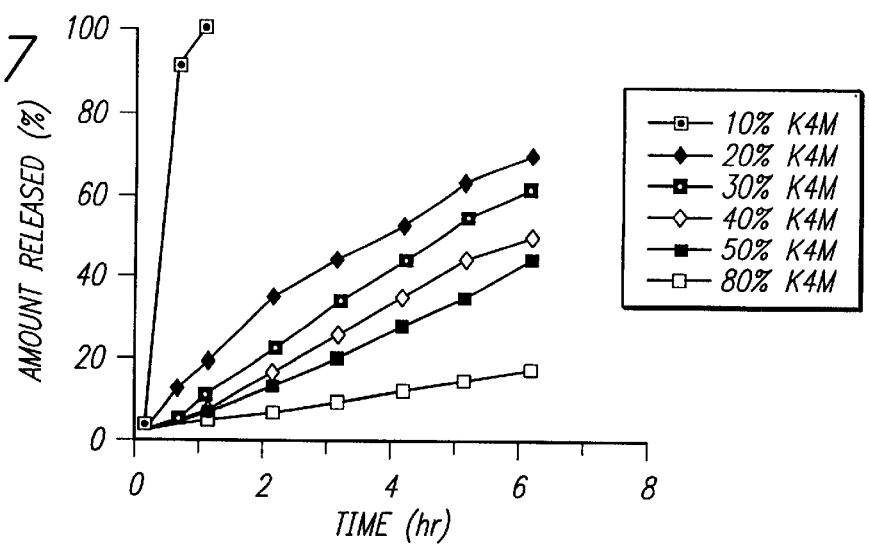
FIG. 7 shows the effect of HPMC concentration on the dissolution rate of carbamazepine.

Results which are seen in FIG. 7 show that increasing the concentration of Methocel K4M in the tablets decreased the release rate of carbamazepine from the matrix.

The increasing concentration of Methocel increased the viscosity and strength of the gel layer formed and thereby decreased the erosion rate of the tablets. Drug release from the matrix followed zero-order release kinetics in the concentration ranges 20–80% Methocel K4M. In a formulation containing 10% Methocel K4M, the tablet disintegrated relatively fast because of the formation of noncontinuous gel layer. A formulation containing 20% Methocel K4M provided an initial small burst effect followed by zero order kinetics.

This study shows and confirms that by changing the amount of the HPMC in the matrix, the drug delivery is conveniently engineered to release the drug in zero-linear release kinetics. As seen in FIG. 7, for example when the 60% release of the drug is desired within 6 hours, 30% concentration of the HPMC K4M is conveniently used. When the lower amount, such as 30% of the drug is to be released in 6 hours, the 50% concentration of the HPMC K4M is selected. When the really slow release of the drug is desired, then the composition of the tablet contains 80% of the HPMC K4M.

B. The Effect of Viscosity Grade of HPMC on the Drug Release Rate from Matrix and on the Dissolution Rate Matrices containing carbamazepine and HPMC of various viscosity grades—Methocel K100LV, Methocel K4M, Methocel K15M and Methocel K100M were prepared as described in Example 2 for preparation of tablets. Two concentrations of the polymer in the matrix were examined, namely 30% (w/w) and 50% (w/w). In matrices containing 30% polymer, lower viscosity grades of Methocel, such as Methocel E15 and Methocel E5 were also examined.

Figure 8:
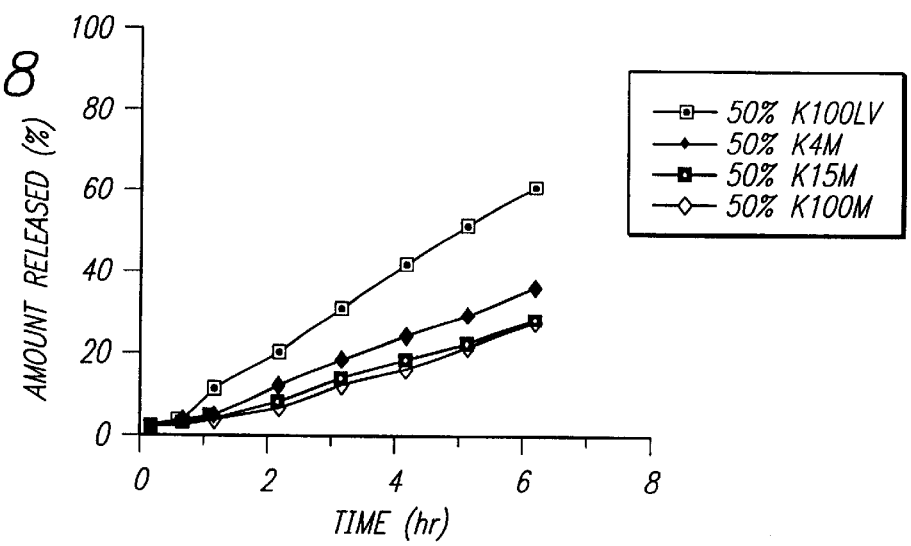
FIG. 8 shows the influence of viscosity grade of Methocel on the dissolution rate of carbamazepine wherein Methocel concentration in the matrix is 50%.
Figure 9:
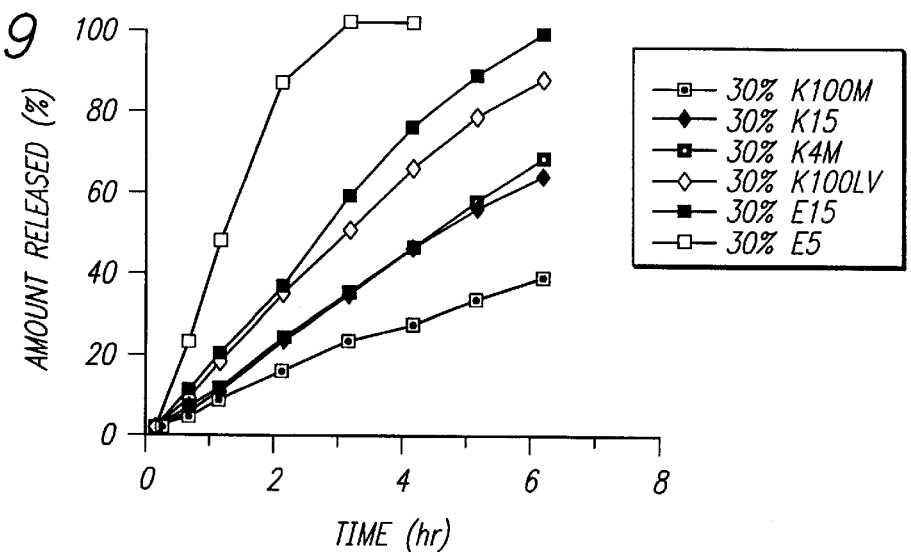
FIG. 9 shows the effect of viscosity grade of Methocel on the dissolution rate of carbamazepine wherein Methocel concentration in the matrix is 30%.

Results are seen in FIGS. 8 and 9. These figures show that carbamazepine release rate from matrices containing Methocel K100LV, a lower viscosity grade of Methocel, was higher than matrices containing Methocel K4M, K15M and K100M.

As seen in FIG. 8, Methocel K100LV (50%) released about 60% of the drug within 6 hours. Carbamazepine release rate was similar from matrices containing 50% Methocel K4M, K15M and K100M.

FIG. 9 shows that when the concentrations of the polymer is lowered to 30%, its viscosity plays a role in the release rate. Lower viscosity grades of Methocel, such as Methocel E15 and Methocel E5, in 30% concentration did show a higher release than those of having a higher viscosity. Drug release from formulations containing the lower viscosity grade of Methocel E5 was the highest, reaching 100% release in 3 hours. Carbamazepine release rate from formulation containing 30% of high viscosity Methocel K100M was slower compared to carbamazepine release from lower viscosity grades of Methocel.

Carbamazepine release rate from the various viscosity grades was by zero-order kinetics.

These results support finding that the formulation and the method of the invention are successful in achieving the sustained zero-order release of which rate can be controlled by proper selection of the polymer and its viscosity.

C. The effect of Incorporation of Additives on Carbamazepine Release Rate

Additives NaCl, PEG 4,000 and PEG 20,000, were sieved through 60 mesh sieve and incorporated into the matrix tablet at concentration of 20% w/w at the expense of the polymer. For these studies, the drug concentration in the matrix was 50%. Tablets containing 30% Methocel K4M, where the total tablet weight was 0.4 g, were also prepared for comparison. The dissolution rate from the matrices was examined as described above in section II.

The incorporation of 20% NaCl, PEG 20,000 or PEG 4,000 into the matrix tablets increased the release rate of carbamazepine in comparison to formulations containing 50% Methocel K4M or 30% Methocel K4M.

Figure 10:
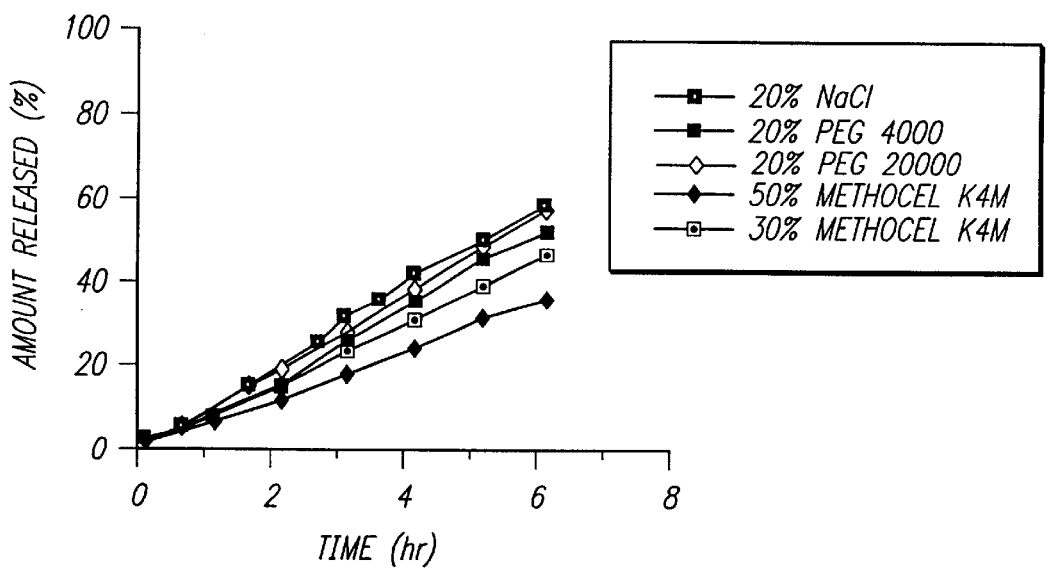
FIG. 10 shows the influence of additives on the release rate of carbamazepine from matrix tablets containing 50% carbamazepine.

As seen in FIG. 10, there was a slight difference in the release rate from the matrices containing the additives. Carbamazepine release rate from tablets containing 20% NaCl was the highest. The incorporation of 20% PEG 4,000 or PEG 20,000 to the matrices caused softening of the tablets when hydrated.

In all these instances, carbamazepine release from the different formulations was by zero-order release kinetics.

This study shows that by adding certain pharmaceutically acceptable additives to the polymer matrix, the release rate can be affected.

D. The Effect of Rotation Speed of the Baskets on the Release Rate

The dissolution rate of matrices containing 40% Methocel K4M were examined using 50, 100 and 200 rpm rotations.

Figure 11:
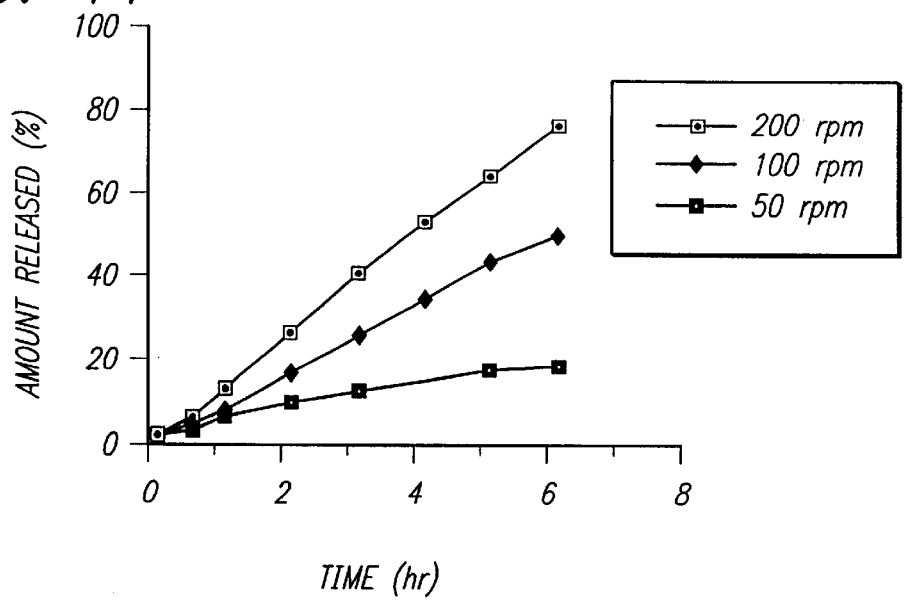
FIG. 11 shows the effect of rotation speed of the baskets on the release rate.

Results are seen in FIG. 11. Increasing the rotation rate of the baskets from 50 to 200 rpm increased the release rate of carbamazepine from the matrix. The reason for the faster release in the case of higher rotation speed appears to lie in the increase rate of matrix dissolution.

As seen in FIG. 11, the highest release of the drug was achieved when 200 rpm rotation speed was used. Carbamazepine release was examined by zero-order kinetics for the different hydrodynamic conditions.

This study shows that the release of the drug from the formulation is affected by hydrodynamic conditions.

E. The Effect of the Medium Composition on Drug Release Rate from the Matrix

The dissolution rate from matrices containing 40% Methocel K4M were examined in medium containing 0.5% SDS and 1% SDS in water.

Figure 12:
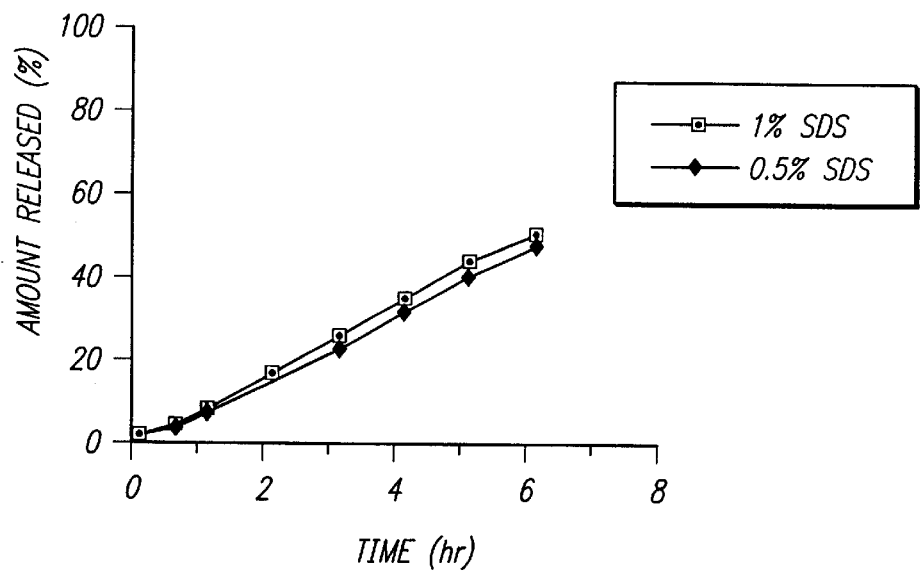
FIG. 12 shows the influence of SDS concentration on carbamazepine release rate from matrix tablets containing 40% Methocel K4M.

Results are seen in FIG. 12. As seen in FIG. 12, carbamazepine release rates were similar in medium containing 1% SDS in water and 0.5% in water. The drug solubility in medium containing 1% SDS in water (3.3 mg/ml) was significantly higher than its solubility in medium of 0.5% SDS in water (1.468 mg/ml).

This shows that drug release from the matrix occurs by erosion of the tablet and the contribution of diffusion to the release mechanism can be neglected.

F. Carbamazepine Release from Matrix Tablets Based on HPMC Containing 400 mg and 600 mg Carbamazepine Matrix tablets containing 400 mg carbamazepine and 30% Methocel K4M were prepared as described. Tablet diameter was 12 mm. Drug release from the matrix was examined as described in Example 3.

Matrix tablets containing 600 mg carbamazepine and 30% Methocel K100LV were prepared similarly. Tablet diameter was 15 mm. Drug release from the matrix was examined as described in Example 3.

Figure 13:
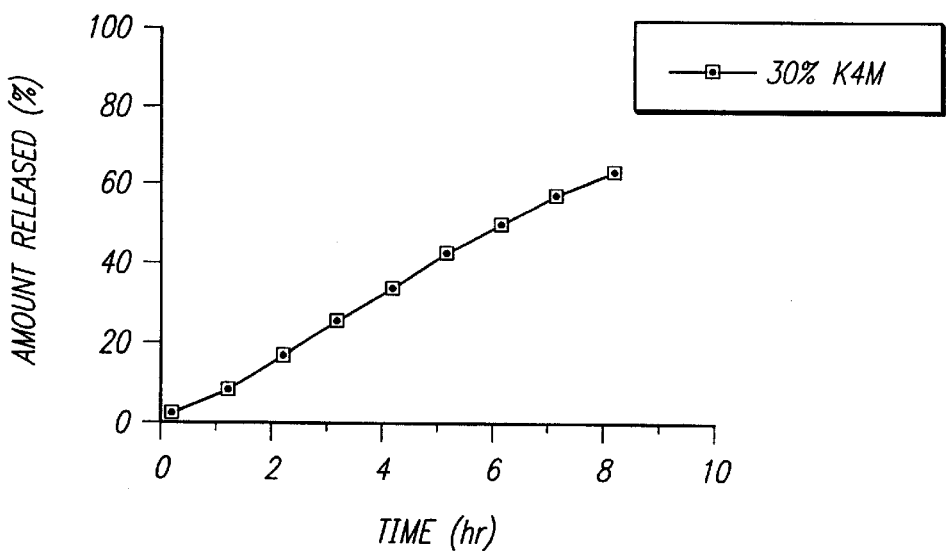
FIG. 13 shows carbamazepine (400 mg) release from a formulation containing 30% Methocel K4M.
Figure 14:
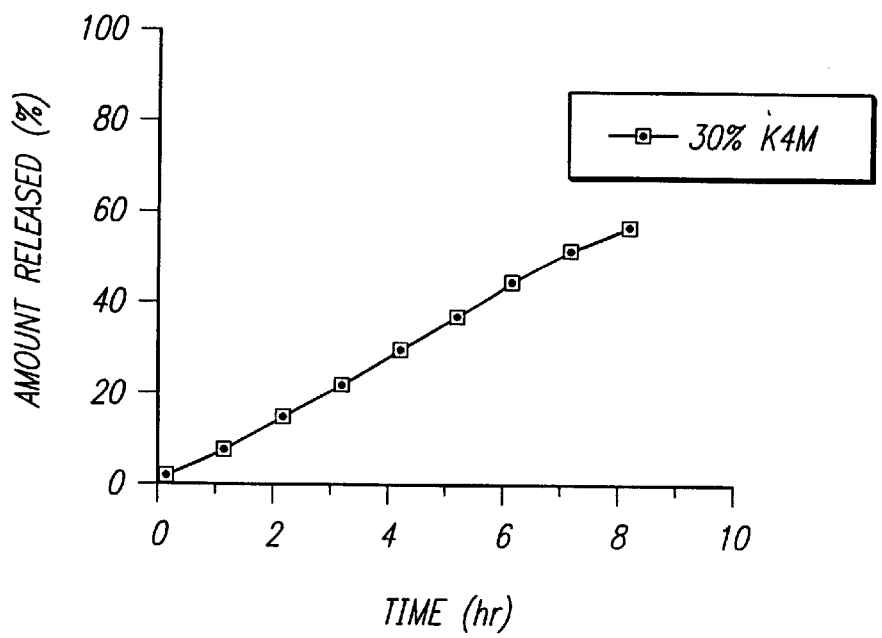
FIG. 14 shows carbamazepine (600 mg) release from a formulation containing 30% Methocel K4M.
Figure 15:
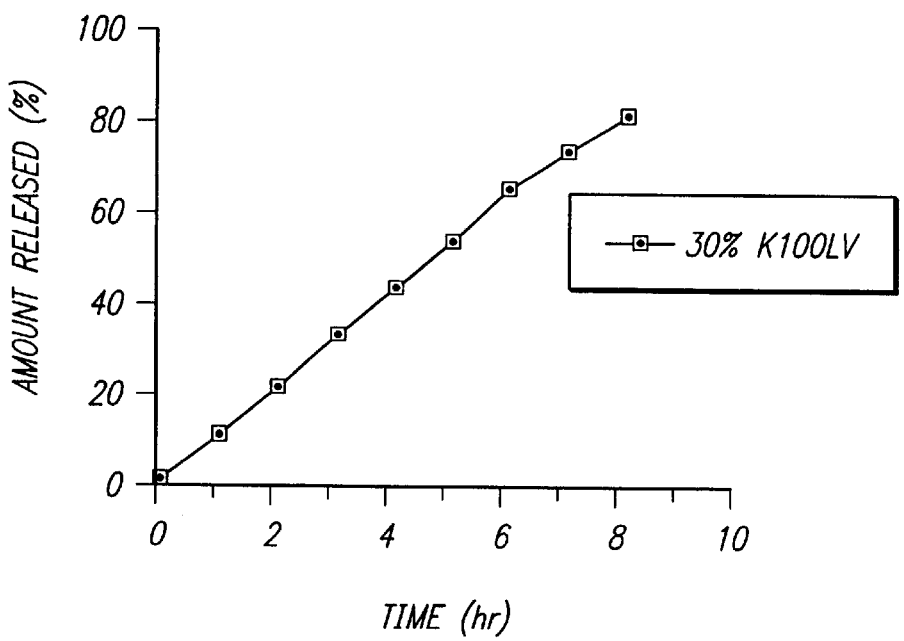
FIG. 15 shows carbamazepine (600 mg) release from a formulation containing 30% Methocel K100LV.

Carbamazepine release from the formulation containing 400 mg and 600 mg was by zero-order kinetics as presented in FIGS. 13–15.

As seen in FIG. 13, the polymer comprising 30% of the Methocel K4M containing 400 mg of carbamazepine released more than 60%, that is about 240 mg of drug in 8 hours.

As seen in FIG. 14, the polymer K4M (30%) containing 600 mg of the drug was able to release 60% (360 mg) of 600 mg of drug in 8 hours.

As seen in FIG. 15, release of the drug (600 mg) was further enhanced by formulating the drug in 30% K100LV, low viscosity polymer resulting in about 80% release of the carbamazepine, that is, about 480 mg of drug was released in 8 hours.

These studies further show that the release-rate depends on the amount of the drug within the polymer as well as on the selected polymer and on its properties and that all these parameters may be advantageously utilized to prepare oral formulations of the drug where the amount of the drug is released in a continuous and sustained manner in zero-order release rate.

G. Erosion Studies

The erosion of matrices containing 30%, 40% and 50% Methocel K4M and 30% of Methocel K100LV were studied. Tablet erosion tests were performed using USP I Basket Method at the same conditions described in dissolution studies. At various times intervals the tablets were removed from the baskets and dried for at least 24 hours at 37° C. until a constant weight was obtained. The percentage of tablet eroded was calculated from the weight loss of the tablets.

Carbamazepine release rate from the different formulations examined followed the rate of matrix dissolution. This shows that drug release is controlled solely by erosion of the tablet.

H. The Influence of HPMC on the Crystal Morphology and Structure of Carbamazepine in the Gel Layer Tablets containing 50% carbamazepine and 50% Methocel K4M were prepared and hydrated in medium containing 1% SDS in water, using tablet dissolution tester at the same conditions used for measurements of the release rate of the drug.

At various time intervals the tablets were removed and the gel layer was peeled, dried at room temperature and analyzed by DSC, X-ray and SEM. For comparison, a suspension containing carbamazepine in 1% SDS water solution was prepared and the crystals obtained were analyzed by DSC, X-ray and SEM.

Analysis of carbamazepine in the gel layer by DSC, X-ray and SEM revealed that the HPMC inhibits the transformation of carbamazepine to carbamazepine dihydrate and that carbamazepine in the gel layer becomes more amorphous. This shows that HPMC interacts with carbamazepine, participates in its crystallization and changes its crystal morphology.

UTILITY

The invention is useful for efficacious and controlled oral delivery of carbamazepine or its derivatives having low water solubility. The drug delivery system has the ability to release the drug from the erodible tablet in zero-order release kinetics.

The delivery system of the invention is useful for delivery of accurate and continuous amounts of the drug where such delivery can be designed by changing the viscosity of the polymer, drug concentration or by other variables described above.

EXAMPLE 1

Assay of the Active Agent

This example describes assay for determination of concentrations of the active agent.

Carbamazepine concentrations were determined spectrophotometrically at 288 nm in 1% sodium dodecyl sulfate (SDS) in water. This medium was selected since it enhances significantly the solubility of the drug. The concentrations were determined from a suitable calibration curve.

EXAMPLE 2

Preparation of Erodible Tablets

This example describes process used for preparation of carbamazepine erodible tablets.

Carbamazepine (200/mg) and HPMC in different amounts were thoroughly mixed using a pestle and a mortar to produce different HPMC/carbamazepine ratios. All tablets contained 200 mg carbamazepine unless otherwise stated.

Cylindrical tablets were prepared by direct compression of drug-polymer blends using a laboratory press fitted with a 10 mm (or 12 mm) flat-faced punch and die set applying a 5 ton force.

When NaCl, PEG 4,000 or PEG 20,000 were incorporated into the dry matrix, they were sieved through a 60 mesh sieve and thoroughly mixed with the drug and polymer using a pestle and mortar.

Hydroxypropyl methylcellulose (HPMC) was added in an amount from 0–99% per tablet (% wt/wt) as indicated in FIGS. 7–12.

EXAMPLE 3

Dissolution Rate Studies

This example describes a process used in dissolution rate studies.

The dissolution rate from the tablets were monitored using tablet dissolution tester (model 7st, Caleva, USA). The USP I Basket Method was used, rotating at 100 rpm in 700 ml medium containing 1% SDS in water maintained at 37° C. The drug levels were monitored spectrophotometrically (Uvicone 930 Kontron spectrophotometer, Switzerland). Dissolution rate studies were performed in triplicate for each batch of tablets.

EXAMPLE 4

Analytical Methods

This example describes analytical methods and equipment used in the studies leading to the invention.

Differential Scanning Calorimetry

The thermal analysis of the samples was performed using a Differential Scanning Calorimeter (DSC, Mettler TA4000 with measuring cell DSC 30E, Switzerland). Samples were measured into aluminum pans. Lids were crimped and holes were made in lids in order to allow dehydration of samples. The thermal behavior of the samples was studied under nitrogen purge at heating rates of 10° C. min$^{-1}$ over a temperature range of 0° C. to 250° C. When the glass transition temperature of HPMC was examined the heating rate was 0.5° C. min$^{-1}$.

X-Ray Diffraction

X-ray powder diffraction of the samples was recorded by Philips automated diffractometer using Cu-K α radiation (40 kV, 35 mA) at a scanning rate of 0.5° per 20 min$^{-1}$.

Scanning Electron Microscopy

Samples of hydrated tablets were sliced across the gel layer. The samples were washed and then treated with increasing concentration of ethanol, 5 minutes at each concentration, for dehydration. In order to complete the dehydration the samples were transferred in solution of freon 113:ethanol with increasing concentrations of freon (25, 50, 75, 100%). The samples with 100% freon were incubated in the hood for 0.5 hour. The cross-sectioned tablets were mounted on stubs and coated with a polaron sputter coater, Model E5100. The film thickness obtained was approximately 75 Å. Scanning electron photomicrographs were recorded using a Philips 505 SEM, applying voltage of 20 V. Samples of powders were coated and analyzed under the same conditions described for the hydrated tablets.

What is claimed is:

1. An erodible oral composition for sustained release delivery of carbamazepine or a derivative thereof at a zero-order release kinetics comprising:

(a) carbamazepine or the derivative thereof;

(b) an erodible polymeric matrix comprising at least one hydrophilic polymer or a mixture of two or more hydrophilic polymers, having viscosity between about 3 and about 100,000 mpa.s (cp) at concentration of 2% at 20° C. and a molecular weight between about 10,000 and about 246,000;

wherein said composition erodes and releases carbamazepine or the derivative thereof in a zero-order release kinetics.

2. The composition of claim 1 wherein said carbamazepine derivative is selected from the group consisting of:

10,11-dihydro-10-oxo-5H-dibenz/b,f/azepine-5-carboxamide/(oxcarbazepine);

10,11-dihydro-10-hydroxy-5H-dibenz/b,f/azepine-5-carboxamide;

10-acetoxy-10,11-dihydro-5H-dibenz/b,f/azepine-5-carboxamide;

10-benzoyloxy-10,11-dihydro-5H-dibenz/b,f/azepine-5-carboxamide;

10-(4-methoxybenzoyloxy)-10,11-dihydro-5H-dibenz/b,f/azepine-5-carboxamide;

10-(3-methoxybenzoyloxy)-10,11-dihydro-5H-dibenz/b,f/azepine-5-carboxamide;

10-(2-methoxybenzoyloxy)-10,11-dihydro-5H-dibenz/b,f/azepine-5-carboxamide;

10-(4-nitrobenzoyloxy)-10,11-dihydro-5H-dibenz/b,f/azepine-5-carboxamide;

10-(3-nitrobenzoyloxy)-10,11-dihydro-5H-dibenz/b,f/azepine-5-carboxamide;

10-(2-nitrobenzoyloxy)-10,11-dihydro-5H-dibenz/b,f/azepine-5-carboxamide;

10-(4-chlorobenzoyloxy)-10,11-dihydro-5H-dibenz/b,f/azepine-5-carboxamide;

10-(3-chlorobenzoyloxy)-10,11-dihydro-5H-dibenz/b,f/ azepine-5-carboxamide;

10-(2-acetoxybenzoyloxy)-10,11-dihydro-5H-dibenz/b,f/ azepine-5-carboxamide;

10-propionyloxy-10,11-dihydro-5-dibenz/b,f/azepine-5-carboxamide;

10-butyryloxy-10,11-dihydro-5H-dibenz/b,f/azepine-5-carboxamide;

10-pivaloyloxy-10,11-dihydro-5H-dibenz/b,f/azepine-5-carboxamide;

10-[(2-propyl) pentanoyloxy]-10,11-dihydro-5H-dibenz/ b,f/azepine-5-carboxamide;

10-[(2-ethyl)hexanoyloxy]-10,11-dihydro-5H-dibenz/b,f/ azepine-5-carboxamide;

10-stearoyloxy-10,11-dihydro-5H-dibenz/b,f/azepine-5-carboxamide;

10-cyclopentanoyloxy-10,11-dihydro-5H-dibenz/b,f/ azepine-5-carboxamide;

10-cyclohexanoyloxy-10,11-dihydro-5H-dibenz/b,f/ azepine-5-carboxamide;

10-phenylacetoxy-10,11-dihydro-5H-dibenz/b,f/azepine-5-carboxamide;

10-(4-methoxyphenyl)acetoxy-10,11-dihydro-5H-dibenz/ b,f/azepine-5-carboxamide;

10-(3-methoxyphenyl)acetoxy-10,11-dihydro-5H-dibenz/ b,f/azepine-5-carboxamide 10-(4-nitrophenyl)acetoxy-10,11-dihydro-5H-dibenz/b,f/ azepine-5-carboxamide;

10-(3-nitrophenyl)acetoxy-10,11-dihydro-5H dibenz/b,f/ azepine-5-carboxamide;

10-nicotinoyloxy-10,11-dihydro-5H-dibenz/b,f/azepine-5-carboxamide;

10-isonicotinoyloxy-10,11-dihydro-5H-dibenz/b,f/ azepine-5-carboxamide;

10-(4-aminobutanoyloxy)-10,11-dihydro-5H-dibenz/b,f/ azepine-5-carboxamide;

10-(2-amino-3-methylbutanoyloxy)-10,11-dihydro-5H-dibenz/b,f/-azepine-5-carboxamide;

10-chloroacetoxy-10,11-dihydro-5H-dibenz/b,f/azepine-5-carboxamide;

10-bromoacetoxy-10,11-dihydro-5H-dibenz/b,f/azepine-5-carboxamide;

10-formyloxy-10,11-dihydro-5H-dibenz/b,f/azepine-5-carboxamide;

10-ethoxycarbonyloxy-10,11-dihydro-5H-dibenz/b,f/ azepine-5-carboxamide;

10-(2-chloropropionyloxy)-10,11-dihydro-5H-dibenz/b,f/ azepine-5-carboxamide;

10,11-dihydro-10-hydroxyimino-5H-dibenz/b,f/azepine-5-carboxamide;

10,11-benzyloxyimino-10,11-dihydro-5H-dibenz/b,f/ azepine-5-carboxamide;

10-acetyloxyimino-10,11-dihydro-5H-dibenz/b,f/ azepine-5-carboxamide;

10,11-dihydro-10-propionyloxyimino-5H-dibenz/b,f/ azepine-5-carboxamide;

10-butyroyloxyimino-10,11-dihydro-5H-dibenz/b,f/ azepine-5-carboxamide;

10,11-dihydro-10-propionyloxyimino-5H-dibenz/b,f/ azepine-5-carboxamide;

10,11-dihydro-10[(1-napthoyloxy)imino]-5H-dibenz/b,f/ azepine-5-carboxamide;

10-benzyloxyimino-10,11-dihydro-5H-dibenz/b,f/ azepine-5-carboxamide;

10,11-dihydro-10-succinoyloxyimino-5H-dibenz/b,f/ azepine-5-carboxamide;

10,11-dihydro-10-glutaroyloxyimino-5H-dibenz/b,f/ azepine-5-carboxamide;

10,11-dihydro-10-isobutoxycarbonyloxyimino-5H-dibenz/b,f/azepine-5-carboxamide;

10,11-dihydro-10-methoxyimino-5H-dibenz/b,f/azepine-5-carboxamide;

10,11-dihydro-10-(S)-(-)-camphanoyloxyimino-5H-dibenz/b,f/azepine-5-carboxamide;

10,11-dihydro-10-[(3-methoxybenzoyloxyimino)]-5H-dibenz/b,f/azepine-5-carboxamide;

10,11-dihydro-10-nicotinoyloxyimino-5H-dibenz/b,f/ azepine-5-carboxamide;

10,11-dihydro-10-ethoxycarbonyloxyimino-5H-dibenz/b, f/azepine-5-carboxamide;

10-butoxycarbonyloxyimino-10,11-dihydro-5H-dibenz/ b,f/azepine-5-carboxamide; and 10-benzyloxycarbonyloxyimino-10,11-dihydro-5H-dibenz/b,f/azepine-5-carboxamide.

3. The composition according to claim 2 wherein said hydrophilic polymer is selected from the group consisting of methyl cellulose, hydroxypropyl methylcellulose, hydroxyethyl cellulose, hydroxypropyl cellulose, hydroxyethyl methylcellulose, carboxymethylcellulose and sodium carboxymethylcellulose.

4. The composition according to claim 3 wherein said polymer is hydroxypropyl methylcellulose.

5. The composition according to claim 4 wherein said matrix is formulated as an erodible tablet.

6. The composition according to claim 5 additionally containing a hydrophobic component.

7. The composition according to claim 6 wherein the hydrophobic component is selected from the group consisting of cellulose derivatives such as ethyl cellulose fats such as glycerol palmitostearate, beeswax, glycowax, castrowax, carnaubawax, glycerol monostearate or stearylalcohol, a hydrophobic polyacrylamide derivative and a hydrophobic methacrylic acid derivative.

8. The composition according to claim 7 wherein hydrophobic cellulose derivative is ethyl cellulose.

9. The composition according to claim 8 additionally containing a pharmaceutically acceptable constituent and additive selected from the group consisting of a protein, arabinogalactan, chitosan, a polysaccharide, a hydrophilic polyacrylamide derivative and a hydrophilic methacrylic acid derivative.

10. The composition according to claim 9 wherein said protein is bovine albumin, human albumin, egg albumin, soy protein, gelatin or casein in the native or denatured state.

11. The composition according to claim 10 wherein said polysaccharide is β-cyclodextran or a starch derivative.

12. The composition according to claim 11 wherein said fat is glycerol palmitostearate, beeswax, glycowax, castrowax, carnaubawax, glycerol monostearate or stearyl alcohol.

13. The composition according to claim 12 further comprising a pharmaceutically acceptable additive selected from the group consisting of a salt, polyethylene glycol and a surfactant.

14. An erodible tablet for oral sustained delivery of carbamazepine or a derivative thereof released from the tablet in a zero-order release kinetics, said tablet comprising carbamazepine or a derivative thereof selected from the group consisting of:

10,11-dihydro-10-oxo-5H-dibenz/b,f/azepine-5-carboxamide/(oxcarbazepine);

10,11-dihydro-10-hydroxy-5H-dibenz/b,f/azepine-5-carboxamide;

10-acetoxy-10,11-dihydro-5H-dibenz/b,f/azepine-5-carboxamide;

10-benzoyloxy-10,11-dihydro-5H-dibenz/b,f/azepine-5-carboxamide;

10-(4-methoxybenzoyloxy)-10,11-dihydro-5H-dibenz/b,f/azepine-5-carboxamide;

10-(3-methoxybenzoyloxy)-10,11-dihydro-5H-dibenz/b,f/azepine-5-carboxamide;

10-(2-methoxybenzoyloxy)-10,11-dihydro-5H-dibenz/b,f/azepine-5-carboxamide;

10-(4-nitrobenzoyloxy)-10,11-dihydro-5H-dibenz/b,f/azepine-5-carboxamide;

10-(3-nitrobenzoyloxy)-10,11-dihydro-5H-dibenz/b,f/azepine-5-carboxamide;

10-(2-nitrobenzoyloxy)-10,11-dihydro-5H-dibenz/b,f/azepine-5-carboxamide;

10-(4-chlorobenzoyloxy)-10,11-dihydro-5H-dibenz/b,f/azepine-5-carboxamide;

10-(3-chlorobenzoyloxy)-10,11-dihydro-5H-dibenz/b,f/azepine-5-carboxamide;

10-(2-acetoxybenzoyloxy)-10,11-dihydro-5H-dibenz/b,f/azepine-5-carboxamide;

10-propionyloxy-10,11-dihydro-5H-dibenz/b,f/azepine-5-carboxamide;

10-butyryloxy-10,11-dihydro-5H-dibenz/b,f/azepine-5-carboxamide;

10-pivaloyloxy-10,11-dihydro-5H-dibenz/b,f/azepine-5-carboxamide;

10-[(2-propyl)pentanoyloxy]-10,11-dihydro-5H-dibenz/b,f/azepine-5-carboxamide;

10-[(2-ethyl)hexanoyloxy]-10,11-dihydro-5H-dibenz/b,f/azepine-5-carboxamide;

10-stearoyloxy-10,11-dihydro-5H-dibenz/b,f/azepine-5-carboxamide;

10-clopentanoyloxy-10,11-dihydro-5H-dibenz/b,f/azepine-5-carboxamide;

10-cyclohexanoyloxy-10,11-dihydro-5H-dibenz/b,f/azepine-5-carboxamide;

10-phenylacetoxy-10,11-dihydro-5H-dibenz/b,f/azepine-5-carboxamide;

10-(4-methoxyphenyl)acetoxy-10,11-dihydro-5H-dibenz/b,f/-azepine-5-carboxamide;

10-(3-methoxyphenyl)acetoxy-10,11-dihydro-5H-dibenz/b,f/-azepine-5-carboxamide;

10-(4-nitrophenyl)acetoxy-10,11-dihydro-5H-dibenz/b,f/azepine-5-carboxamide;

10-(3-nitrophenyl)acetoxy-10,11-dihydro-5H-dibenz/b,f/azepine-5-carboxamide;

10-nicotinoyloxy-10,11-dihydro-5H-dibenz/b,f/azepine-5-carboxamide;

10-isonicotinoyloxy-10,11-dihydro-5H-dibenz/b,f/azepine-5-carboxamide;

10-(4-aminobutanoyloxy)-10,11-dihydro-5H-dibenz/b,f/azepine-5-carboxamide;

10-(2-amino-3-methylbutanoyloxy)-10,11-dihydro-5H-dibenz/b,f/-azepine-5-carboxamide;

10-chloroacetoxy-10,11-dihydro-5H-dibenz/b,f/azepine-5-carboxamide;

10-bromoacetoxy-10,11-dihydro-5H-dibenz/b,f/azepine-5-carboxamide;

10-formyloxy-10,11-dihydro-5H-dibenz/b,f/azepine-5-carboxamide;

10-ethoxycarbonyloxy-10,11-dihydro-5H-dibenz/b,f/azepine-5-carboxamide;

10-(2-chloropropionyloxy)-10,11-dihydro-5H-dibenz/b,f/azepine-5-carboxamide;

10,11-dihydro-10-hydroxyimino-5H-dibenz/b,f/azepine-5-carboxamide;

10,11-benzyloxyimino-10,11-dihydro-5H-dibenz/b,f/azepine-5-carboxamide;

10-acetyloxyimino-10,11-dihydro-5H-dibenz/b,f/azepine-5-carboxamide;

10,11-dihydro-10-propionyloxyimino-5H-dibenz/b,f/azepine-5-carboxamide;

10-butyroyloxyimino-10,11-dihydro-5H-dibenz/b,f/azepine-5-carboxamide;

10,11-dihydro-10-pivaloyloxyimino-5H-dibenz/b,f/azepine-5-carboxamide;

10,11-dihydro-10-[(1-napthoyloxy)imino]-5H-dibenz/b,f/azepine-5-carboxamide;

10-benzoyloxyimino-10,11-dihydro-5H-dibenz/b,f/azepine-5-carboxamide;

10,11-dihydro-10-succinoyloxyimino-5H-dibenz/b,f/azepine-5-carboxamide;

10,11-dihydro-10-glutaroyloxyimino-5H-dibenz/b,f/azepine-5-carboxamide;

10,11-dihydro-10-isobutoxycarbonyloxyimino-5H-dibenz/b,f/azepine-5-carboxamide;

10,11-dihydro-10-methoxyimino-5H-dibenz/b,f/azepine-5-carboxamide;

10,11-dihydro-10-(S)-(—)-camphanoyloxyimino 5H-dibenz/b,f/azepine-5-carboxamide;

10,11-dihydro-10-[(3-ethoxybenzoyloxyimino)]-5H-dibenz/b,f/azepine-5-carboxamide;

10,11-dihydro-10-nicotinoyloxyimino-5H-dibenz/b,f/azepine-5-carboxamide;

10,11-dihydro-10-ethoxycarbonyloxyimino-5H-dibenz/b,f/azepine-5-carboxamide;

10-butoxycarbonyloxyimino-10,11-dihydro-5H-dibenz/b,f/azepine-5-carboxamide; and 10-benzyloxycarbonyloxyimino-10,11-dihydro-5H-dibenz/b,f/azepine-5-carboxamide formulated in a polymeric matrix comprising a mixture of at least one hydrophilic polymer and at least one hydrophobic polymer, wherein said hydrophilic polymer having viscosity between about 3 and about 100,000 mPa.s(cp) at concentration of 2% at 20° C. and a molecular weight between about 10,000 and about 246,000;

wherein said composition erodes and releases carbamazepine or the derivative thereof in a zero-order release kinetics.

15. The tablet according to claim 14 wherein said hydrophilic polymer is selected from the group consisting of methyl cellulose, hydroxypropyl methylcellulose, hydroxyethyl cellulose, hydroxypropyl cellulose, hydroxyethyl methylcellulose, carboxymethylcellulose and sodium carboxymethylcellulose and wherein said hydrophobic polymer is selected from hydrophobic cellulose derivatives, fats, hydrophobic polyacrylamide and polyamide derivatives, and hydrophobic methacrylic acid derivatives.

16. The formulation tablet according to claim 15 additionally containing proteins, arabinogalactan, chitosan, polysaccharides, hydrophilic polyacrylamide and hydrophilic methacrylic acid derivatives.

17. The tablet according to claim 16 further comprising a pharmaceutically acceptable additive selected from salts, polyethylene glycol and surfactants.

18. The formulation tablet according to claim 17 formulated in dosage unit form.

19. A method for a sustained and controlled zero-order release kinetics of drug delivery comprising:

(a) preparation of erodible formulation in form of an erodible tablet, erodible capsule or erodible granules comprising a matrix consisting of carbamazepine or a carbamazepine derivative in admixture with a hydrophilic polymer having a viscosity between about 3 and about 100,000 mpa.s cp concentration of 2% at 20 or in admixture with a mixture of the hydrophilic and a hydrophobic polymer; and (b) administering said erodible formulation orally to a patient wherein upon contact of the erodible formulation with aqueous condition of the digestive system, the formulation erodes at a zero-order release kinetics and releases carbamazepine or a derivative thereof in the zero-order release kinetics.

* * * * *